United States Patent
Hubscher et al.

(10) Patent No.: US 11,813,446 B2
(45) Date of Patent: Nov. 14, 2023

(54) METHODS OF FOR IMPROVEMENT OF LOWER URINARY TRACT FUNCTION

(71) Applicant: University of Louisville Research Foundation, Inc., Louisville, KY (US)

(72) Inventors: Charles S. Hubscher, Louisville, KY (US); Susan J. Harkema, Louisville, KY (US); April N. Herrity, Peewee Valley, KY (US); Yangsheng Chen, Louisville, KY (US); Claudia Angeli, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 450 days.

(21) Appl. No.: 16/840,353

(22) Filed: Apr. 4, 2020

(65) Prior Publication Data
US 2020/0316378 A1   Oct. 8, 2020

Related U.S. Application Data

(60) Provisional application No. 62/829,901, filed on Apr. 5, 2019.

(51) Int. Cl.
*A61N 1/36* (2006.01)
*A61N 1/05* (2006.01)

(52) U.S. Cl.
CPC ....... *A61N 1/36007* (2013.01); *A61N 1/0551* (2013.01)

(58) Field of Classification Search
CPC .............. A61N 1/36007; A61N 1/0551; A61N 1/0553; A61N 1/3615; A61N 1/36171;
(Continued)

(56) References Cited

U.S. PATENT DOCUMENTS

| | | | |
|---|---|---|---|
| 9,358,394 B2 | 7/2016 | Steinke et al. | |
| 2010/0274310 A1* | 10/2010 | Boggs, II | A61N 1/0524 607/41 |

(Continued)

OTHER PUBLICATIONS

International Search Report and Written Opinion, dated Jul. 1, 2020—International Application No. PCT/US2020/026761.
(Continued)

*Primary Examiner* — Mark W. Bockelman
(74) *Attorney, Agent, or Firm* — Dentons Bingham Greenebaum LLP; Brian W. Chellgren

(57) ABSTRACT

The present invention relates to methods for improvement in lower urinary tract function in an individual with neurogenic urological dysfunction through epidural stimulation of the spinal cord. In certain embodiments, the methods comprise applying a pattern of epidural electrical stimulation to the spinal cord of an individual with impaired lower urinary tract under stimulation parameters sufficient to improve the storage of fluid in the bladder, sensations of fullness and/or emptying, detrusor over-activity, high detrusor pressure, voiding the bladder, transitioning from a storage state to a voiding state, and decreasing detrusor-external urethral sphincter dyssynergia. In certain embodiments, additional patterns of epidural electrical stimulation may be applied simultaneously, such as to maintain a normotensive cardiovascular state of the individual.

23 Claims, 16 Drawing Sheets

(58) Field of Classification Search
CPC ............ A61N 1/36185; A61N 1/36062; A61N 1/36117
See application file for complete search history.

(56) References Cited

U.S. PATENT DOCUMENTS

| | | |
|---|---|---|
| 2018/0229036 A1 | 8/2018 | Harkema et al. |
| 2018/0229038 A1 | 8/2018 | Burdick et al. |
| 2018/0256906 A1* | 9/2018 | Pivonka ............... A61N 1/0553 |
| 2020/0230417 A1* | 7/2020 | Phillips .............. A61N 1/36031 |

OTHER PUBLICATIONS

Supplementary European Search Report for Application No. EP 20 78 5058 to the University of Louisville Research Foundation, dated Oct. 27, 2022.

* cited by examiner

METHODS OF FOR IMPROVEMENT OF LOWER URINARY TRACT FUNCTION

CROSS-REFERENCE TO RELATED APPLICATIONS

This application claims the benefit of U.S. provisional patent application Ser. No. 62/829,901, filed Apr. 5, 2019, for METHODS FOR RESTORATION OF BLADDER CONTROL, incorporated herein by reference.

GOVERNMENT RIGHTS

This invention was made with government support under R01HD080205 and OT2OD024898 awarded by the National Institutes of Health. The government has certain rights in the invention.

FIELD OF THE INVENTION

The present invention relates to methods for improvement in lower urinary tract (LUT) function in an individual with neurogenic urological dysfunction through epidural stimulation of the spinal cord. In certain embodiments, the methods comprise applying a pattern of epidural electrical stimulation to the spinal cord of an individual with impaired LUT under stimulation parameters sufficient to improve the storage of fluid in the bladder, sensations of fullness and/or emptying, detrusor over-activity, high detrusor pressure, voiding the bladder, transitioning from a storage state to a voiding state, and decreasing detrusor-external urethral sphincter dyssynergia. In certain embodiments, additional patterns of epidural electrical stimulation may be applied simultaneously, such as to maintain a normotensive cardiovascular state of the individual.

BACKGROUND

Urological dysfunction consistently remains an area of highest priority following spinal cord injury (SCI) or other neurological disorders and diseases, as it has a dramatic impact on overall health and quality of life, yet clinical treatments focus on symptom-centric approaches. Functional impairments of the LUT after SCI manifest as a failure to both store and empty the bladder, greatly impacting daily life. While current management strategies are necessary for urological maintenance, they oftentimes are associated with life-long side effects.

Following SCI, volitional control to all or a portion of the LUT is impaired. Initially, there is a period of bladder areflexia and urinary retention followed by the emergence of spinally-mediated voiding reflexes and bladder hyperreflexia. Subsequently, involuntary, uninhibited reflex detrusor contractions occur at low volumes of stored urine and can lead to loss of continence. Additionally, as the detrusor muscle contracts, the external urethral sphincter simultaneously reflexively contracts, causing detrusor-sphincter dyssynergia. Uncoordinated activity between the bladder muscle and its sphincter produces high intravesical pressure that can lead to vesicoureteral reflux, potentially damaging both the lower and upper urinary tracts. Thus the most common, long-term management of neurogenic disorders of micturition commonly includes clean intermittent catheterization and conservative pharmacological therapy to decrease bladder over-activity, high intravesical pressure, and/or proximal urethral resistance while increasing bladder capacity.

Despite the necessary conventional approaches to manage LUT storage and detrusor over-activity related dysfunctions, commonly prescribed anti-cholinergics have side effects such as dry mouth and constipation that exacerbate existing bladder/bowel issues. Chronic daily catheterization is also associated with scarring and strictures, cystitis, formation of false tracts, frequent urinary tract infections, and renal disease. Additionally, in individuals with cervical injuries having compromised hand function, self-intermittent catheterization is not always a viable option, leading to caregiver dependence or indwelling catheter management. Thus, there is a need for additional measures with fewer side effects, but ones that also target functional LUT recovery, as LUT dysfunction still ranks among the top disorders affecting quality of life.

SUMMARY

Embodiments of the present invention relate to spinal cord epidural stimulation (scES) as a therapy to improve LUT in individuals with neurological disorders, injuries, or disease states impairing urinary function, such as individuals having suffered SCI. or other neurological disorders, injuries, or disease states associated with impaired LUT function.

SCI disrupts normal control of bladder function by interrupting both afferent transmission to higher centers and efferent drive to lower spinal levels that modulate output to the LUT. As a result, aberrant reflexes develop below the level of a spinal lesion to produce uncoordinated activity leading to incontinence, inefficient bladder emptying and high pressure. This disclosure indicates that scES targeting the autonomic outflow to the LUT is sufficient to induce improved functionality of the LUT, including consistent increases in voiding efficiency, perhaps influencing detrusor contraction strength and external urethral sphincter relaxation.

Activity-based recovery training (ABRT), including locomotor training (LT—step and stand training), are interventions which have emerged as safe and effective therapies for post-SCI motor deficits and have been shown to provide additional benefits to autonomic function. Furthermore, the combination of ABRT plus scES has not only enhanced the execution of motor tasks in clinically motor complete SCI individuals but has also resulted in improved physiologic outcomes such as temperature regulation, bladder, and sexual function. Despite reports on enhanced urologic outcomes following scES with ABRT, the effect of scES alone on LUT function in humans has herein been specifically targeted, as the stimulation parameters used for scES with ABRT are typically directed toward recovery of motor and cardiovascular function.

The effects of scES alone has been evaluated (Scientific Reports publication, Herrity et al., 2018) specifically for LUT function in a clinically motor complete SCI individual. Mapping using different anode/cathode configurations, spinal cord locations, and stimulation frequencies for bladder effects during repeated cystometry evaluation revealed an effective lumbosacral scES electrode configuration that improved reflexive voiding efficiency in this individual. This configuration was then re-tested in four additional individuals (3 AIS A, 1 AIS B), already implanted with spinal cord epidural stimulators. The efficacy of scES to excite the spinal cord circuitry at the lower lumbosacral region and facilitate neural output to the bladder to improve storage and/or elimination is demonstrated.

The LUT mapping study, published in Scientific Reports 2018, was undertaken for sixteen sessions over the course of four months in an individual with chronic, motor complete SCI. Varying combinations of stimulating cathode electrodes were initially tested during filling cystometry resulting in the identification of an effective configuration for reflexive bladder emptying at the caudal end of the electrode array. Subsequent systematic testing of different frequencies at a fixed stimulus intensity and pulse width yielded lowest post-void residual volumes at 30 Hz. These stimulation parameters were then tested in four additional research participants and found to also improve reflexive voiding efficiency. Taken together with SCI studies on step, stand, voluntary motor control and cardiovascular regulation, these findings further corroborate that scES has an all-encompassing potential to increase the central state of excitability, allowing for the control of multiple body functions, including the urological system.

It will be appreciated that the various systems and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

A better understanding of the present invention will be had upon reference to the following description in conjunction with the accompanying drawings.

DETAILED DESCRIPTION OF THE PREFERRED EMBODIMENTS

Scientific Reports Published Study

Figure 1:
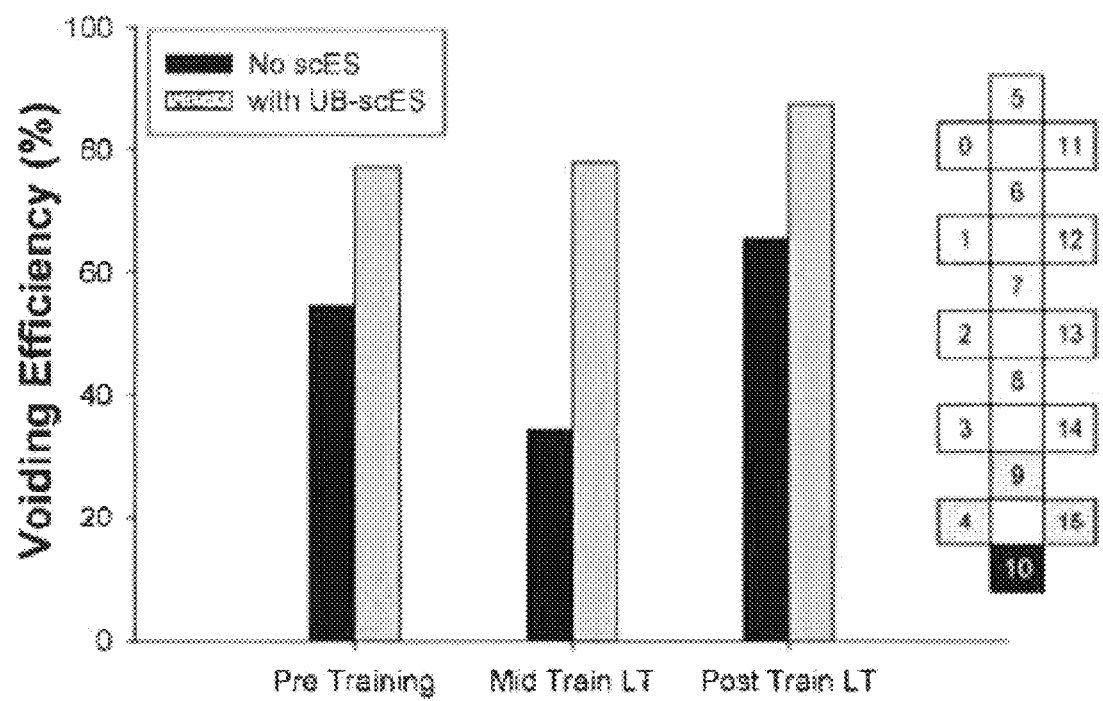
FIG. 1 depicts a graph of bladder voiding efficiency, with and without urinary bladder scES (UB-scES), performed following epidural stimulator implantation at pre-ABRT, mid-ABRT, and post-ABRT time points showing improved voiding efficiency with UB-scES. The electrode configuration used during bladder filling cystometry is illustrated to the right of the graph.

The participant, B23, is a 31-year old male (age at first pre-training Urodynamics assessment), who was enrolled in a research study conducted at the University of Louisville investigating the effects of activity-based training in combination with scES on the recovery of lower limb motor function. As part of that study, he received an epidural spinal cord stimulator (Medtronic, RestoreAdvanced) and a 16-electrode array (Medtronic, 5-6-5 Specify) that was surgically placed at the spinal segments L1-S1, 3.3 years after traumatic SCI because of a mountain biking accident (see Table 1 for project timeline). Prior to and following implantation of the spinal cord epidural stimulator, he received intensive LT (stand/step and stand/step in combination with scES, respectively). The current bladder mapping experiment was conducted after B23 completed the LT+scES study on the recovery of lower limb motor function and does not represent selective data pooling from a larger study. Table 1 provides a context for how the bladder mapping project was initiated.

TABLE 1

Timeline of therapy progression for participant B23.

| Time Point | Pre Implant Post Training LT | Surgery | Post Implant Pre Training LT | Post Implant Mid Training LT | Post Implant Post Training LT | Home Training | 6 month Follow Up |
|---|---|---|---|---|---|---|---|
| Training Sessions | 40 Stand 40 Step | | | 40 Stand-scES 40 Step-scES | 40 Stand-scES 40 Step-scES | Stand-scES | Stand-scES |
| Frequency | Each on same day; 5 d/wk | | | Each on alternating days; 5 d/wk | Each on alternating days; 5 d/wk | Daily; 5 d/wk | Daily; 5 d/wk |
| Assessment | Uro-dynamics | | Uro-dynamics | Uro-dynamics | Uro-dynamics | Bladder Mapping | Uro-dynamics |
| Duration | 3 months | 4 weeks | | 5 months | 4 months | 1 month | 6 months |

"d/wk", days per week;
LT, locomotor training;
scES, spinal cord epidural stimulation Clinical Evaluation. Research participant B23 received a clinical evaluation prior to this study to assess motor and sensory status. Two clinicians independently performed the International Standards for Neurological Classification of Spinal Cord Injury in order to classify the participant's injury using the ASIA (American Spinal Injury Association) Impairment Scale (AIS). Following the assessment, he was classified as AIS B (pinprick and light-touch present below the lesion), with a neurological level of injury at C5. A physical examination also was performed by a clinician for medical clearance, ensuring participation safety using the following inclusion criteria: (1) stable medical condition; (2) epidural stimulator implanted at the lumbosacral spinal cord; and (3) bladder dysfunction as a result of SCI. Note that B23 had never received Botox injections for management of bladder dysfunction but had a suprapubic catheter. Individuals with suprapubic catheters tend to have low capacities, which was the case for B23. Multiple fill-void cycles could thereby be accomplished in each 90-minute cystometry session (a common fill rate of 20 ml/minute was used).

Activity-based recovery training. Prior to epidural stimulator implant, research participant B23 underwent 80 sessions of LT (Table 1), which included stand and step training, with the goal of achieving the positive adaptations induced by activity-based training alone before the beginning of LT with scES. Following implantation, participant B23 continued 160 sessions of locomotor training (stand plus step training). Stand and step training were performed on separate days for the initial 80 sessions, alternating the intervention between days. Following the midpoint, a second session per day was added. One day a week, every 2-3 weeks, was added until reaching 5 days per week of stand and step training on the same day, alternating the training intervention between the morning and afternoon, with each session lasting 1 hour, 5 days per week and always performed with scES.

Urodynamics. Data were obtained from standard urodynamic evaluations with recommendations from the International Continence Society. All studies were performed by the same registered nurse using the Aquarius® LT (Laborie, Williston, VT) urodynamic investigation system. Bladder medication (10 mg Oxybutynin twice a day) was ceased 24 hours prior to every urodynamics session. The procedure was discussed with the research participant, including any risks and potential side effects not limited to infection and/or bleeding. Cystometry was performed in the supine position via a single sensor, dual channel catheter (7 Fr, T-DOC® Air-Charged™, Laborie, Williston, VT) with continuous filling of sterile, body-temperature water (37° C.) at a fixed slow rate of 20 ml/min. Abdominal pressure was measured via a rectal balloon catheter (7 Fr, T-DOC® Air-Charged™, Laborie, Williston, VT). Pelvic floor electromyography (EMG) (Neotrode II, Laborie, Williston, VT) was recorded using surface patch EMG electrodes and a grounding pad was placed on a bony prominence, usually the hip or knee. Detrusor pressures were calculated by subtracting the intra-abdominal pressure from the intra-vesical pressure. B23 was asked to cough to verify intra-abdominal catheter position, instructed to communicate filling sensations as follows: First sensation of fullness (FSF)—the first sense that there is fluid in the bladder; First desire (FD)—the feeling that one would void at the next convenient moment; Strong desire (SD)—a compelling need to void that is less comfortable to postpone; Capacity (C)—the feeling that voiding cannot be delayed any longer. The volume of water and bladder pressure was recorded. Uninhibited bladder contractions also were identified. The research participant was asked to empty his bladder while voiding bladder pressures were recorded.

Blood pressure (BP), heart rate (HR) and oxygen saturation were recorded every minute during urodynamics using an automated sphygmomanometer (DinamapVl00; GE Medical Systems, Fairfield, CT). Baseline BP recordings were obtained in the supine position prior to urodynamic testing. Any signs and self-reported symptoms of autonomic dysreflexia were documented and observed throughout testing. Bladder filling was ceased if any of the following conditions were observed: (1) spontaneous urine leakage, (2) infused volume≥600 mL, (3) sustained high intravesical filling pressure 2:40 cmH2O (if present for greater than 15 seconds) or (4) autonomic dysreflexia as evidenced by a sudden rapid rise in blood pressure from baseline and/or intolerable symptoms (such as a pounding headache). A post-fill BP recording was captured to ensure BP values returned to baseline.

Spinal Cord Epidural Stimulation. Spinal cord epidural stimulation targeting the urinary bladder (UB-scES) and related parts of the LUT was administered during cystometry through a multi-electrode array (Medtronic Specify 5-6-5, Restore ADVANCED) implanted in the epidural space over spinal cord segments L1-S1 (at vertebral levels T11-T12). An implanted package containing stimulating circuits, rechargeable battery, and wireless communication activates the electrodes (16 platinum electrodes arranged in three columns of 5-6-5). The pattern of electrically active electrodes, as well as electrode voltage, stimulating frequency, and stimulating pulse width can be remotely programmed. Guidelines for selecting electrodes were based on our previous work. Briefly, the participant underwent 16 urodynamic sessions, in which a maximum of 6 fill/void cycles were performed on each occasion. The establishment of stimulating parameters was initiated by using a global configuration, which is defined by (1) selecting cathodes (−) and anodes (+) at opposite ends of the array in order to generate either a caudal or rostral flow of current. (2) Stimulating cathode electrodes at the caudal end of the array targeted the lower lumbosacral region of the cord for bladder emptying. (3) Electrode configurations were then modified by reducing the distance between the cathodes and anodes. (4) Using a fixed frequency (beginning at 5 Hz) and pulse width (450 µs), voltage was ramped up slowly (0.1 V increments) while the effects on motor evoked responses were monitored. The ramp up on voltage continued until muscle contraction (present in one or multiple muscles: gluteus maximus, vastus lateralis, biceps femoris, tibialis anterior, and soleus) was present as a result of the stimulation (then lowered 0.1 V—stimulation intensity targeted to be just below motor response threshold). The bladder was then filled with sterile water at a fixed 20 ml per minute rate while the stimulation was on and bladder pressure was monitored. Using the identified electrode configuration, three separate urodynamic sessions were subsequently performed to evaluate the effects of varying frequency (in the order of: no scES, 5, 15, 30, 45, or 60 Hz) on voiding efficiency values. Each session always included one cycle without the use of scES for baseline comparison. To distinguish between a targeted stimulation effect on bladder emptying versus repeated cystometry subsequently resulting in larger bladder volumes, a fill cycle without the use of UB-scES was also conducted at the end of a frequency response testing session. The time for each fill/void cycle (approximately 6 minutes) as well as the time interval between each fill/void cycle (approximately 5 minutes) was kept consistent throughout testing. Given the intensity ramp-up phase of UB-scES added time prior to filling, the interval time period from testing with scES to no scES (i.e. when frequency was reversed and no scES was tested last) was also set at 5 minutes to be consistent. Testing of B23's effective voiding efficiency electrode configuration was conducted in four additional scES implanted research participants (A60—T4 AIS A; A68—C5 AIS A; B21—C4 AIS B; A41—C4 AIS A) for three fill-void cycles that included one without stimulation and two using different frequencies (selected based upon the results from B23). In this instance, the fill cycle order was: no scES, UB-scES at 5 Hz, UB-scES at 30 Hz.

Analysis. Bladder capacity was calculated as the volume of leaked or voided fluid plus any residual amount removed from the bladder. Voiding efficiency was calculated as: [volume voided/(volume voided+residual volume)×100]. Compliance was calculated by dividing the volume change ($\Delta V$) by the change in detrusor pressure ($\Delta Pdet$) during that change in bladder volume and was expressed in ml/cm $H_2O$. The intravesical pressure (Pves) at which involuntary expulsion of water/urine from the urethral meatus was observed was considered the detrusor leak point pressure (DLPP). Maximum detrusor pressure (MDP) was identified as the peak detrusor pressure during the voiding phase of the cystometrogram. Detrusor pressures were calculated by subtracting the intra-abdominal pressure from the intra-vesical pressure.

Cystometry was conducted just prior to training and repeated just after completion of the 80 LT training sessions. Following 80 LT sessions, B23's voiding efficiency improved from 21.9% to 68.5% by the post-training time point. Cystometry was then repeated after epidural stimulator implant, just prior to the next training period (post implant, pre-training), again at mid-training and finally at the post-training time point. The first fill/void cycle was performed without scES and then immediately followed by a fill/void cycle using UB-scES. Selection of electrode configurations targeted the lower region of the array to generate a stimulation zone near the pelvic parasympathetic outflow.

FIG. 1 illustrates the increased gains in voiding efficiency with the use of UB-scES targeting urinary bladder emptying as compared to voiding efficiency values achieved without the use of scES at each post-implant time point. Voiding efficiency values are presented, with and without the use of UB-scES during filling cystometry. Three separate urodynamic assessments were performed following epidural stimulator implantation: pre-training, mid-training, and at the post-training time point. Each time point tested bladder emptying with and without scES. The electrode configuration used during bladder filling cystometry is illustrated to the right of the graph (16-electrodes numbered from 0-15 in the 5-6-5 array). A narrow configuration was initially selected with cathode stimulation (black (−) electrode, 30 Hz, 450 µs) isolating the distal array and anode selection (grey (+) electrodes, inactive electrodes in white) surrounding the targeted stimulation region. At each time point, voiding efficiency improved with scES. These results are for one participant.

At B23's post-implant, pre-training time point, the initial fill/void cycle was performed without the use of scES, indicating maintenance of the acquired pre-implant voiding efficiency value near 60%. The added effect of stimulation alone is immediately apparent as the use of UB-scES in the next fill/void cycle increased voiding efficiency to 77%. By post-implant, post-training, voiding efficiency reached 87.5%, approximating the recommended bladder emptying range established by the International Continence Society (ICS) guidelines (>90% or less than 25 ml post-void residual volume).

Figure 2:
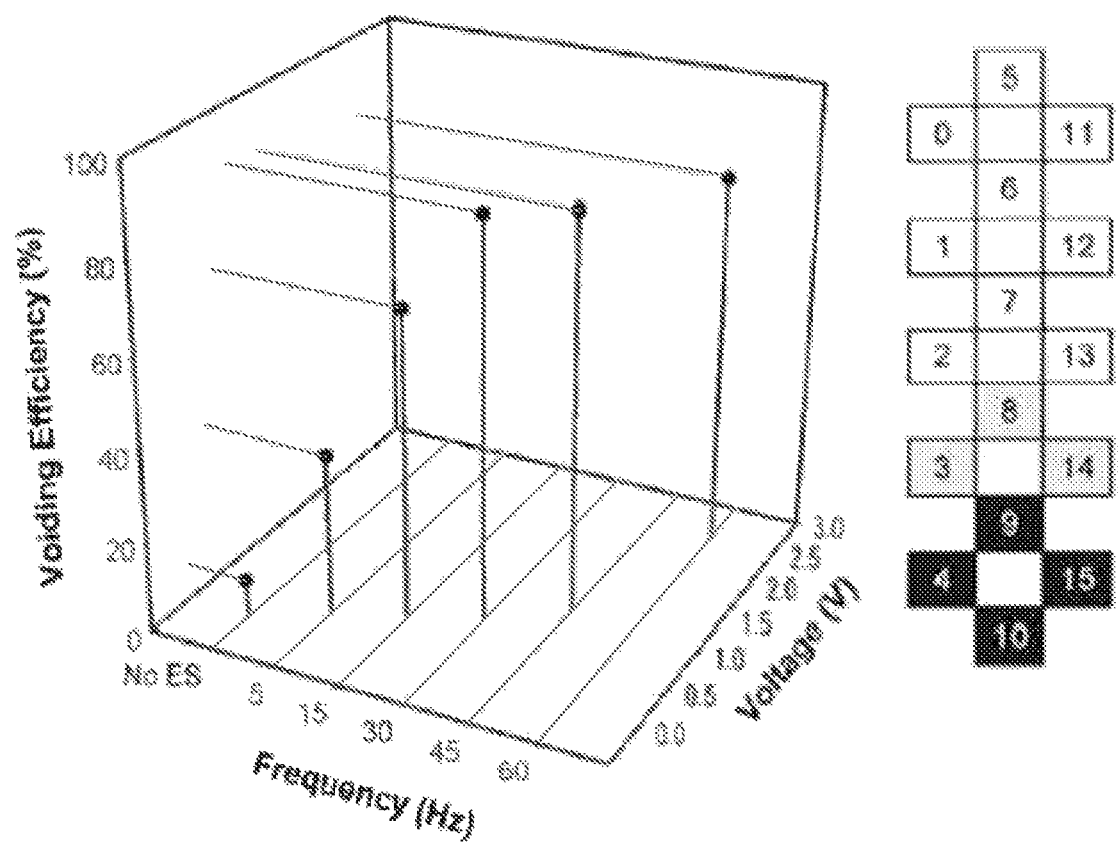
FIG. 2 depicts a graph of voiding efficiency as related to frequency and amplitude of scES showing frequency and intensity dependent effects of electrical stimulation. The electrode configuration used during bladder filling cystometry is illustrated to the right of the graph.

Given the extent of the post-implant increases in voiding efficiency values with the use of UB-scES in B23, we designed bladder mapping assessments aimed at enhancing lower lumbosacral stimulation for bladder emptying. Various stimulating electrode combinations (including at the upper end of the array) were tested over a period of 4 months involving 16 sessions as only one configuration could be examined per fill-void cycle. Note that the participant was not engaged in any LT over the 4-month period. Testing included an expansion of the number of stimulating electrodes at the lower end of array (FIG. 2 diagram) from the combination used initially (as shown in FIG. 1) which yielded the greatest voiding efficiency values as it likely drives the stimulation deeper towards the sacral (S2-4) micturition center. This stimulating array was then tested systematically with five UB-scES frequencies (5, 15, 30, 45 and 60 Hz) during six fill/void reflex cycles (one cycle without stimulation) and repeated in two separate urodynamic sessions for a total of 18 cycles. The results are illustrated graphically in FIG. 2, with the means from the three separate urodynamic sessions for six fill/void reflex cycles represented. Frequency, varied at sub-motor threshold voltage levels, was most effective for voiding efficiency at 30 Hz (88.1±1.1%). Importantly, across all 18 fill/void cycles and frequencies tested, detrusor leak point pressure (22. 1±4.0 cm$H_2O$) and maximum detrusor pressure (29.0±4.0 cm$H_2O$) were both within recommended guidelines established for upper and lower urinary tract preservation. When scES was not used, bladder pressure also remained within normal limits (24.3±14.2 cmH₂O). Note that the one cycle from each session that was performed without the use of scES had the lowest efficiency (8.3±4.6%). The electrode configuration used during bladder filling cystometry is illustrated in FIG. 2 to the right of the graph with an expanded cathode selection (black (−) electrodes) targeting the lumbosacral region (anode (+) selection in grey, inactive electrodes in white). Frequency, varied at voltage subthreshold levels, was most effective for voiding efficiency at 30 Hz (88.1±1.1%). Note that voiding efficiency ~90% is considered within normal limits for lower and upper urinary tract preservation. These results are for one participant.

Figure 3:
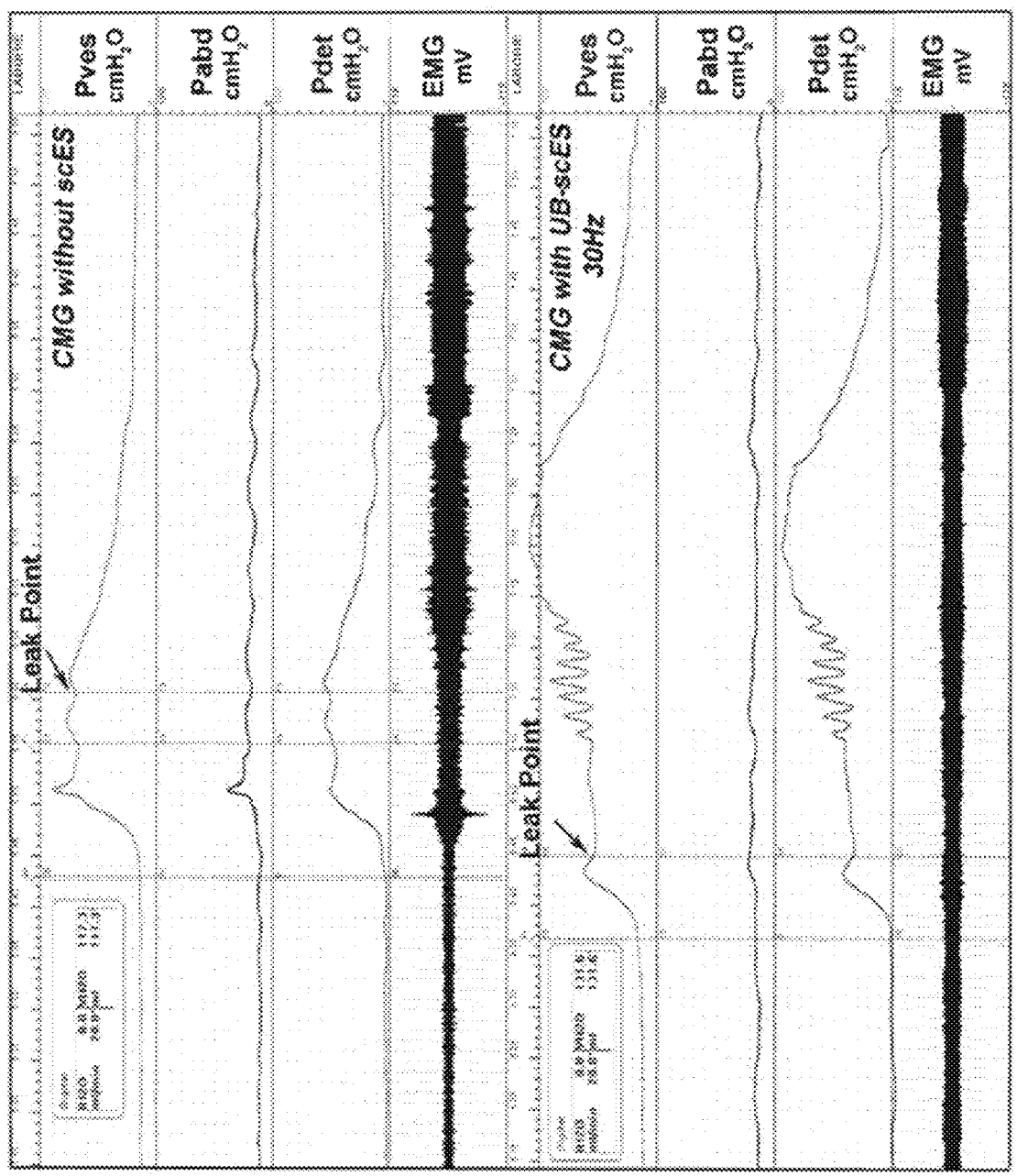
FIG. 3 depicts a pair of cystometrogram (CMG) recordings without UB-scES (top panel) and with UB-scES (bottom panel) at 30 Hz showing the effectiveness of UB-scES.

The area under the contraction curve was assessed for differences between filling without scES relative to UB-scES at 30 Hz (2239.3±373.4 vs 2647.8±1692.9 cmH$_2$O$^2$). Area under the curve, the contraction duration, and filling capacity trended toward an increase with UB-scES at 30 Hz (see FIG. 3); however, the average increase in these parameters across all trials at 30 Hz alone as well as across each frequency tested was not significant when compared to cystometry without scES, likely due to an n=1 test. The range of capacity values were relatively similar across frequencies tested and as compared to no scES: 121.0±7.8 ml—5 Hz; 139.3±11.0 ml—15 Hz; 113.3±13.6 ml—30 Hz; 102.3±24.3 ml—45 Hz; 125.0±14.4 ml—60 Hz versus 111.0±13.4 ml—no scES. Area under the curve demonstrated more variability across all other frequencies tested (3282.7±1177.8—5 Hz; 2531.3±765.5—15 Hz; 2916.0±636.4—45 Hz; 20S8.8±40.6—60 Hz). The greater area evident at 5 Hz stems from a sustained bladder contraction during one fill/void cycle that resulted in a minimal leak (35.8±9.6%). Surface EMG activity obtained during B23's cystometry using UB-scES displayed a quiescent pattern of activation timed to the detrusor contraction (peak of 23.7 mV) compared to an asynchronous firing pattern (peak of 80.3 m V) that would limit emptying during cystometry without scES (FIG. 3). Note that electrode configurations in both the upper lumbar (5−/0−/6−/11−/1−/12−//7+/2+/13+) and middle lumbar (7−/2−/8−/13−//3+/9+/14+/1+/6+/12+) regions of the array were assessed with repeated cystometry and did not result in greater gains in voiding efficiency as compared to the lower lumbosacral region for this research participant [57.9±21.1% (upper) and 68.S±12.2% (middle) versus 88.1±1.1% (lower)]. The bladder contraction during cystometry without scES coincided with an increased pattern of EMG activity as compared to UB-scES at 30 Hz. Note that the fill volume without stimulation was 117.3 ml (capacity of 137 ml and a post-void residual of 132 ml) and 131.6 ml with stimulation (capacity of 139 ml and a post-void residual of 14 ml). Note that total volume is greater than infused volume, as urine is being produced throughout the testing time period.

Figure 4:
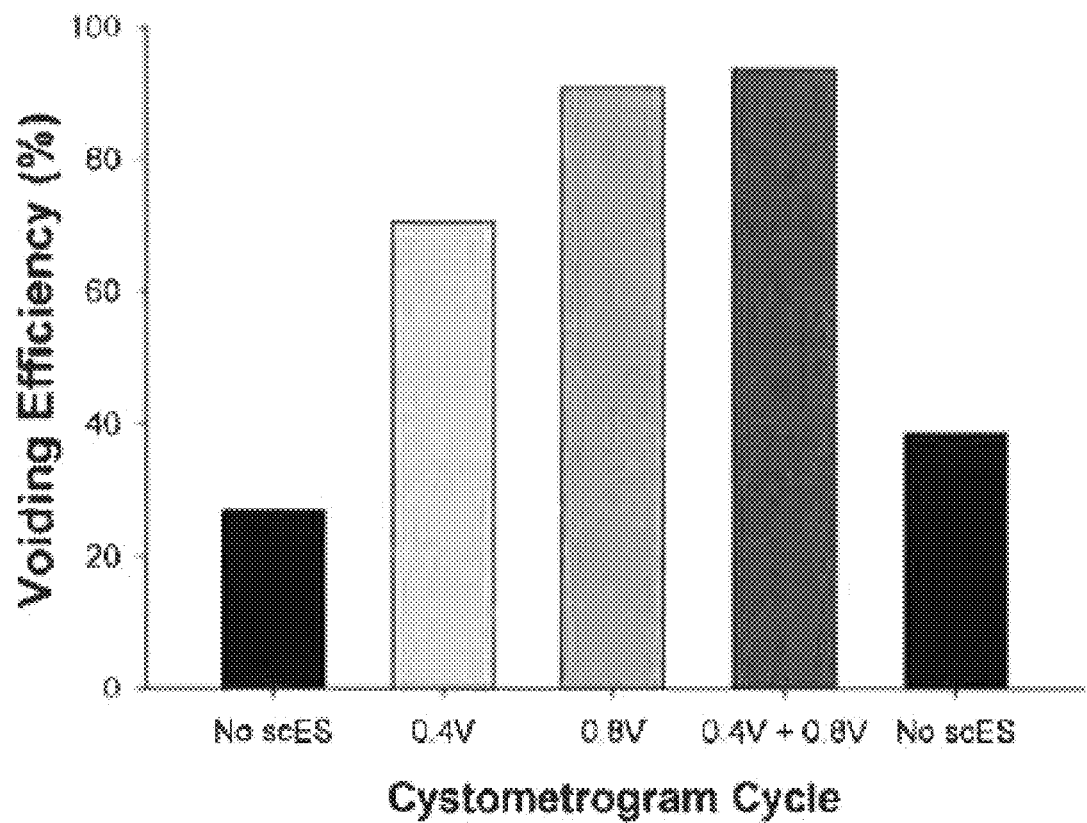
FIG. 4 depicts a chart comparing voiding efficiency as determined by CMG with sub-motor threshold voltage variation during scES showing return to pre-stimulation baseline values upon offset.

Referring now to FIG. 4, research Participant B23 returned for an additional evaluation 6 months after completing the bladder mapping study. The same location/electrode numbers and optimal frequency (30 Hz; per FIG. 2) were used during this assessment except voltage was varied (sub-motor threshold 0.8 V and half the intensity, 0.4 V). The sequence for five fill-void cycles during the 90-minute session was no scES, 0.4 V, 0.8 V, an assessment of the dual program RestoreAdvanced capability (Program 1 at 0.4 V during filling then changing to Program 2 at 0.8 V upon onset of urge to mimic the concept of having one ongoing set of parameters for storage and then switching to void parameters at an appropriate time), followed by a second cycle with stimulation off. The first fill/void cycle performed without the use of scES yielded a low voiding efficiency (27.2%) (FIG. 4). The voiding efficiency outcome was 0.8 V>0.4 V>no scES. Having a lower threshold (0.4 V) running continuously and immediately ramping to a higher threshold once desire to void was recognized did not alter the voiding efficiency to the 0.8 V stimulus. Interestingly, bladder capacity was not altered with this sequence of repetitive fills and scES (103 ml, first cycle versus 98 ml, fifth cycle), indicating the effect was limited to bladder emptying. The last fill/void cycle without scES demonstrates the effect of stimulation alone as voiding efficiency returned toward the initial pre-stimulation value. The electrode configuration used in this experiment was LS/SI region (10−/4−/15−/9−113+/8+/14+), 30 Hz, 450 µs.

Figure 5:
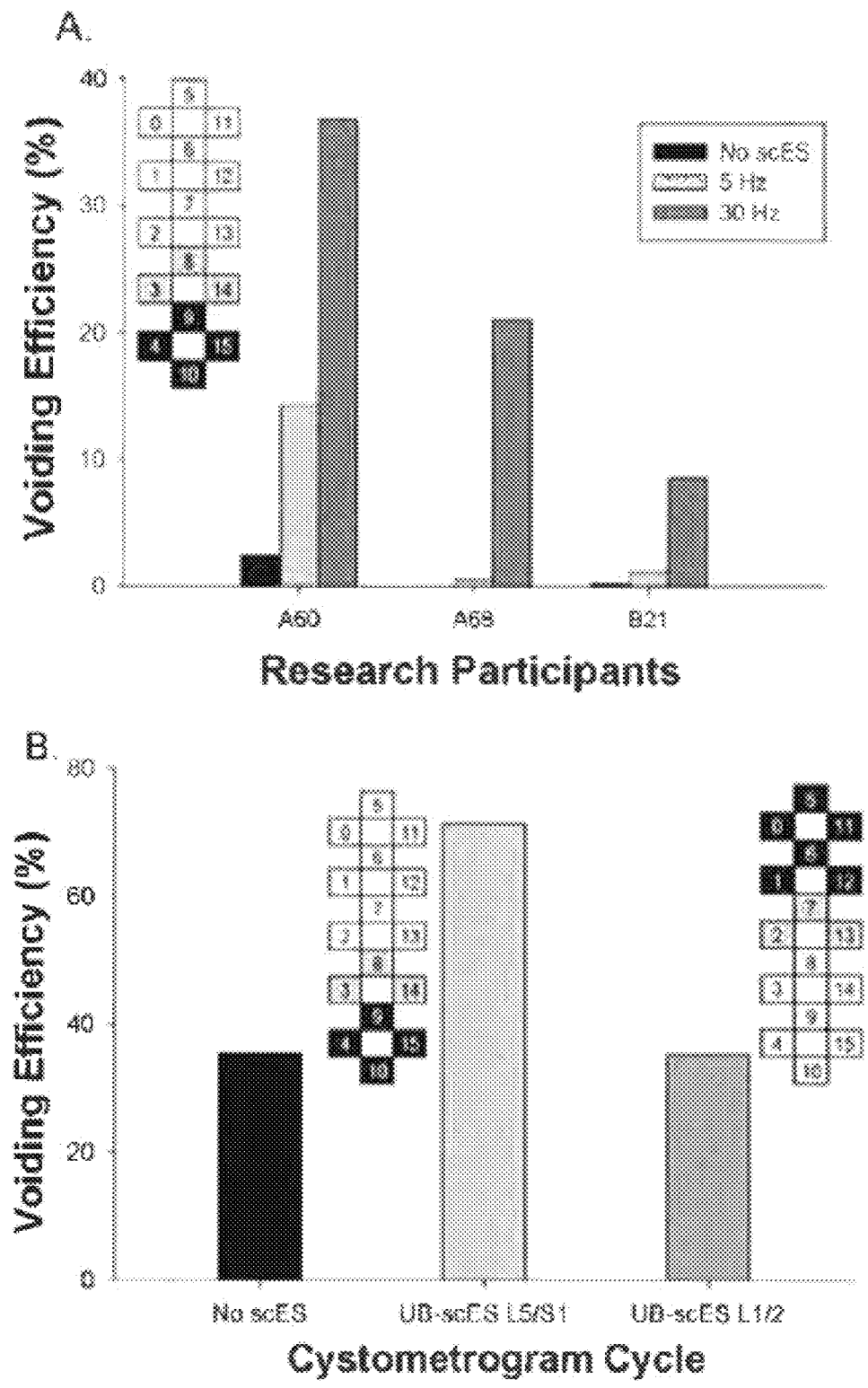
FIG. 5 depicts the positive effects of UB-scES conducted in four additional participants showing improvements in voiding efficiency using the same effective stimulation configuration. Panel A depicts a chart comparing voiding efficiency for three participants with no scES, scES at 5 Hz, and scES at 30 Hz. The electrode configuration used is displayed, and is the same as used in FIG. 2. Panel B depicts a chart showing the location-specific effect of scES for voiding efficiency.

To examine the efficacy of the lower lumbosacral configuration found to be effective for voiding in B23, UB-scES using that configuration (10−/4−/15−/9−//3+/8+/14+) was conducted in four additional research participants during their urodynamic assessments (note that the three participants shown in FIG. 5, panel A, all perform intermittent catheterization for bladder management, whereas the participant shown in FIG. 5, panel B, has a suprapubic catheter). These four participants were male, with an average 6.5±1.9 years post-injury (at the time of the post-training urodynamic assessment). They each were participating in the scES studies assessing the impact of task-specific training (step-scES, stand-scES, voluntary motor training—Vol-scES, and cardiovascular training—CV-scES) on both the motor and autonomic systems. The first fill/void cycle for each cystometry event was performed without the use of scES, with little to no leak in each participant (FIG. 5, panel A). For three of the four participants, three fill/void cycles were examined in a 90-minute session.

The effective electrode configuration for research participant B23 was tested during the second and third fill/void cycle using two different frequencies, 5 Hz and 30 Hz. Note that an increase in voiding efficiency was demonstrated again with scES, with 30 Hz providing a greater increase than 5 Hz, which occurred in both AIS A and B participants. In a fourth participant (FIG. 5, panel B, A41, AIS A and a neurological level of injury at C4), the lower end of the electrode array (L5/S1, 10−/4−/15−/9−//3+/8+/14+) was targeted during urodynamics using the effective voiding efficiency configuration as well as the upper end of the electrode array (L1/L2, 5−/0−/6−/11−/1−/12−//7+/2+/13+). The first fill/void cycle was performed without the use of scES, demonstrating low voiding efficiency output. The next fill/void cycle utilized the same effective lower lumbosacral configuration and stimulation parameters (30 Hz, 450 µsec) as B23, resulting in a doubling of the initial, pre-stimulation voiding efficiency value. The last fill/void cycle targeted the upper lumbar region using multi-electrode configurations (30 Hz, 450 µsec) focusing on the L1/2 region, resulting in low voiding efficiency, equivalent to the pre-stimulation voiding efficiency value, indicating that scES of the lower lumbosacral region was effective for bladder emptying while scES of the upper region was not.

Discussion. Given the initial participant's relatively small bladder capacity due to the presence of a suprapubic catheter as well as initial bladder emptying gains with LT alone and in combination with UB-scES, the focus of the current mapping study was on improving voiding efficiency. Multiple consistent and repeated fill/voiding cycles could be performed during urodynamics due to the participant's low capacity, facilitating the investigation of potential configurations and effective stimulation parameters. The objective was to determine if an effective electrode configuration and stimulation parameter(s) could be achieved with UB-scES to promote more efficient bladder emptying in persons having a motor complete SCI. Mapping for bladder function with different electrode configurations during repeated cystometry revealed increases in the efficiency of the reflexive void with values within recommended clinical guidelines. The electrode combination at the lower end of the stimulator array (L5/S1 region—(10−/4−/15−/9−//3+/8+/14+), optimized at 30 Hz in one individual, was then tested in four more individuals who showed improvements in bladder emptying as well. However, three of the four participants never demonstrated voiding efficiency greater than 50%, one as low as 10% indicating that the results are highly patient specific (FIG. 5, panel A).

Initial use of scES targeted improvements in stepping, standing, and voluntary movement in response to provided task-specific sensory cues in motor complete SCI. Unexpected off-target gains to other physiological systems such as bladder, sexual function, and temperature regulation became evident, although these multiple autonomic changes developed even though the stimulation parameters were aimed at influencing the motor system and the execution of specific motor tasks. Based on these outcomes, we proceeded to systematically and objectively evaluate participants via urodynamic assessments prior to and following task-specific training interventions, including the use of scES. We have previously shown that locomotor training alone was sufficient to induce significant improvements in multiple bladder parameters, such as increased capacity, voiding efficiency, detrusor contraction duration as well as decreased detrusor leak point pressure. These overall urological improvements reported previously also include participant B23. We now demonstrate in this study that the use of scES alone, without additional training, can promote increases in voiding efficiency. An effective stimulation frequency and electrode configuration at the lower end of the stimulator array over the L5/S1 region yielded voiding efficiency values close to the standard threshold of 90%, or even better (as seen for B23 in FIG. 4, at 93.8%). Although voiding efficiency shifted closer to normal in the four participants who were later assessed, the configuration used in these assessments was one deemed effective for B23. Note, three of the five participants exhibited much more reduced voiding efficiency responses than B23. We know from mapping studies for stand and step training interventions that optimal configurations vary from individual to individual, necessitating mapping.

The use of scES described herein may be an effective alternative approach which mechanistically may involve indirect activation of the same neural networks for bladder function. However, it remains to be shown if some features like incontinence management will occur with scES. Also, the current results of low voiding efficiency in three out of the five participants will require further investigations. Although scES requires implantation surgery, which may be a drawback for some individuals to consider, given that the consequences of SCI affect multiple systems, this intervention may also benefit other autonomic systems controlling cardiovascular, respiratory, bowel, sexual function and temperature regulation. Thus, the potential multi-system benefits of scES have the capability for dramatically impacting quality of life. Furthermore, once a participant's device is programmed with effective stimulation programs, the ability for on-demand device use becomes particularly essential for initiating particular tasks, such as triggering the voiding phase of micturition.

Although the mechanisms associated with the improvements in voiding efficiency shown here are not entirely known, optimizing the level of excitability of the nervous system through scES may foster a priming effect at the spinal cord, thus modulating the excitability of spinal reflexes. The ability of the spinal cord to interpret both incoming sensory input and residual descending drive with sufficient responses to that information is important in this regard. The central activation and excitation driven by the scES parameters may influence neural output to the detrusor muscle, causing a more sustained contraction in comparison to the quick bursting contractions that are typical of hyperreflexia which limits bladder emptying. Modulation of reflex mechanisms controlling micturition can arise from spinal convergence of somatosensory input leading to a suppression of the bladder guarding reflex and resulting in decreased urethral sphincter contractions and improved voiding efficiency. The bladder is also a unique visceral organ in that, in addition to various reflex mechanisms that exist to modulate both the storage and voiding phases, it also exhibits predominately voluntary regulation, unlike other visceral organs such as the heart and gastrointestinal tract, which receive tonic neural control. With ample descending drive, scES may promote a decreased pressure system for the lower urinary tract.

If voiding with UB-scES can be achieved, residual volumes may not be low enough to avoid catheterization, although the number of times could still be reduced, perhaps just to the morning and night-time, giving more flexibility during daily activities and eliminating disruption of sleep. However, regardless of the extent of the effect that will be obtained, any improvement in bladder function, even incremental, would have a dramatic impact on health and quality of life for those suffering the lifelong consequences of neurologic injury.

Study Submitted for Publication

Figure 6:
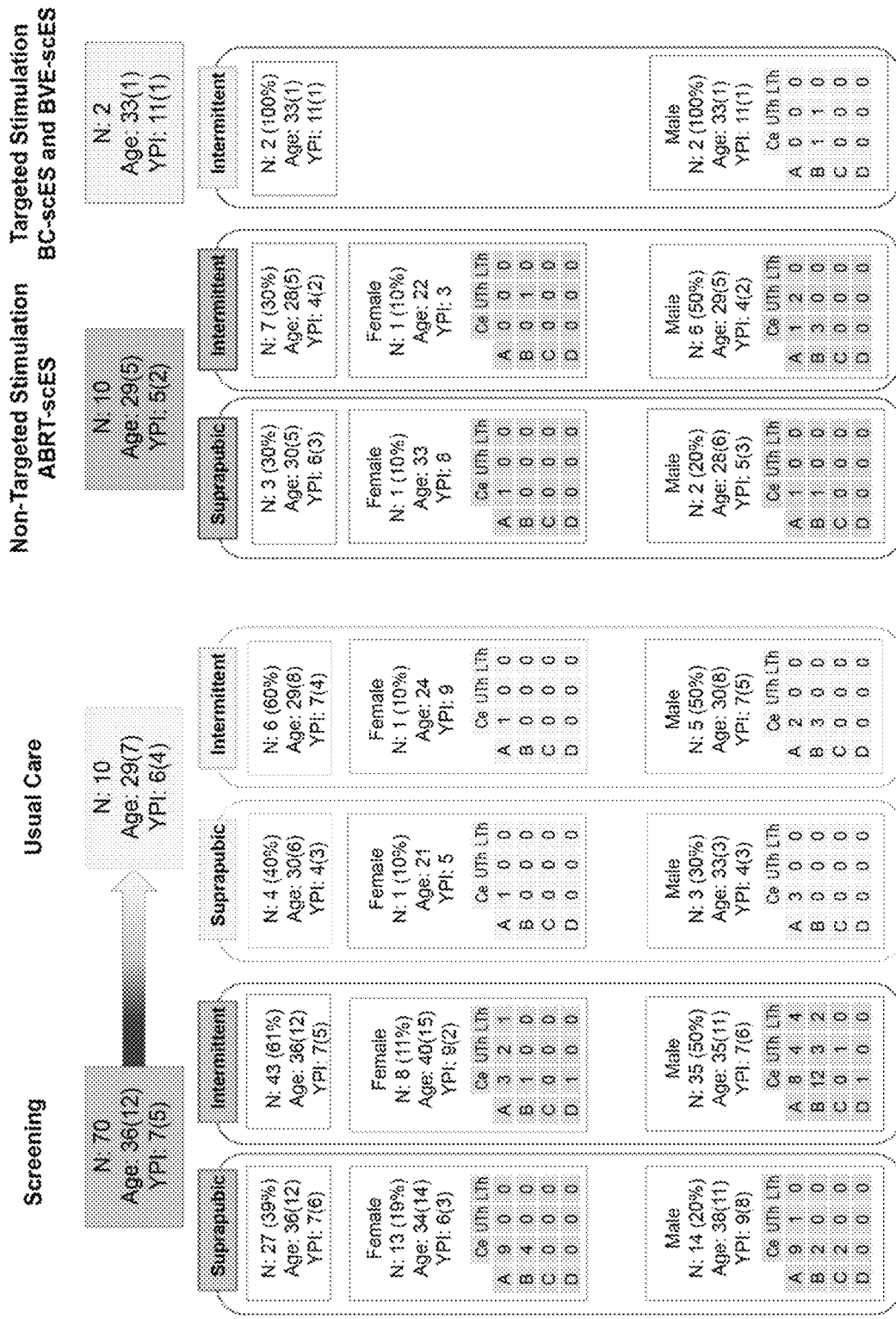
FIG. 6 depicts the demographic characteristics of research participants in another scES study currently under review for publication.

The clinical characteristics of 70 screened research participants are provided in FIG. 6, including the 10 usual care individuals who were assessed a second time after conducting their daily lives for an approximately three-month period of time without any intervention or change in routine. Screened participants included both males and females using either intermittent catheterization or suprapubic catheterization for bladder emptying. Average (standard deviation) of age (in years), years post injury (YPI), level of injury (cervical [Ce], upper thoracic [UTh; T1-6], and lower thoracic [LTh; T7-12]) and severity of injury using the American Spinal Injury Association Impairment Scale (AIS) (motor complete [A and B] and motor-incomplete [C and D]) are given for each group. Almost all the individuals with suprapubic catheters, which were significantly fewer relative to intermittent catheterization (p<0.01), had cervical levels of injury (96%; limited hand dexterity). Note that for the ABRT-scES group, categorical values were determined from the time at which each participant presented for the post-implant, pre-training urodynamic assessment. Also, all provided AIS scores were from assessments just prior to study initiation. (ABRT, Activity-based recovery training; BC, Bladder capacity; BVE, Bladder voiding efficiency; scES, spinal cord epidural stimulation; YPI, years' post-injury). Note that the 10 usual care participants encompass a group from the 70 screened participants who qualified for other programs in the center and thus, underwent additional measurements prior to their interventions. They are separately characterized, as their data is being used for pre/post comparison to the 10 pre/post ABRT-scES intervention group. Since these participants received a follow-up assessment after screening, their progress was observed during this usual care window.

Both cohorts have similar characteristics, including 80/20% male/female ratio, which closely represents the national statistical report of sex prevalence in SCI. None of the participants altered their method of bladder emptying throughout the study. For the two participants receiving targeted bladder scES, age, time since injury, and bladder emptying method were similar.

Figure 7A:
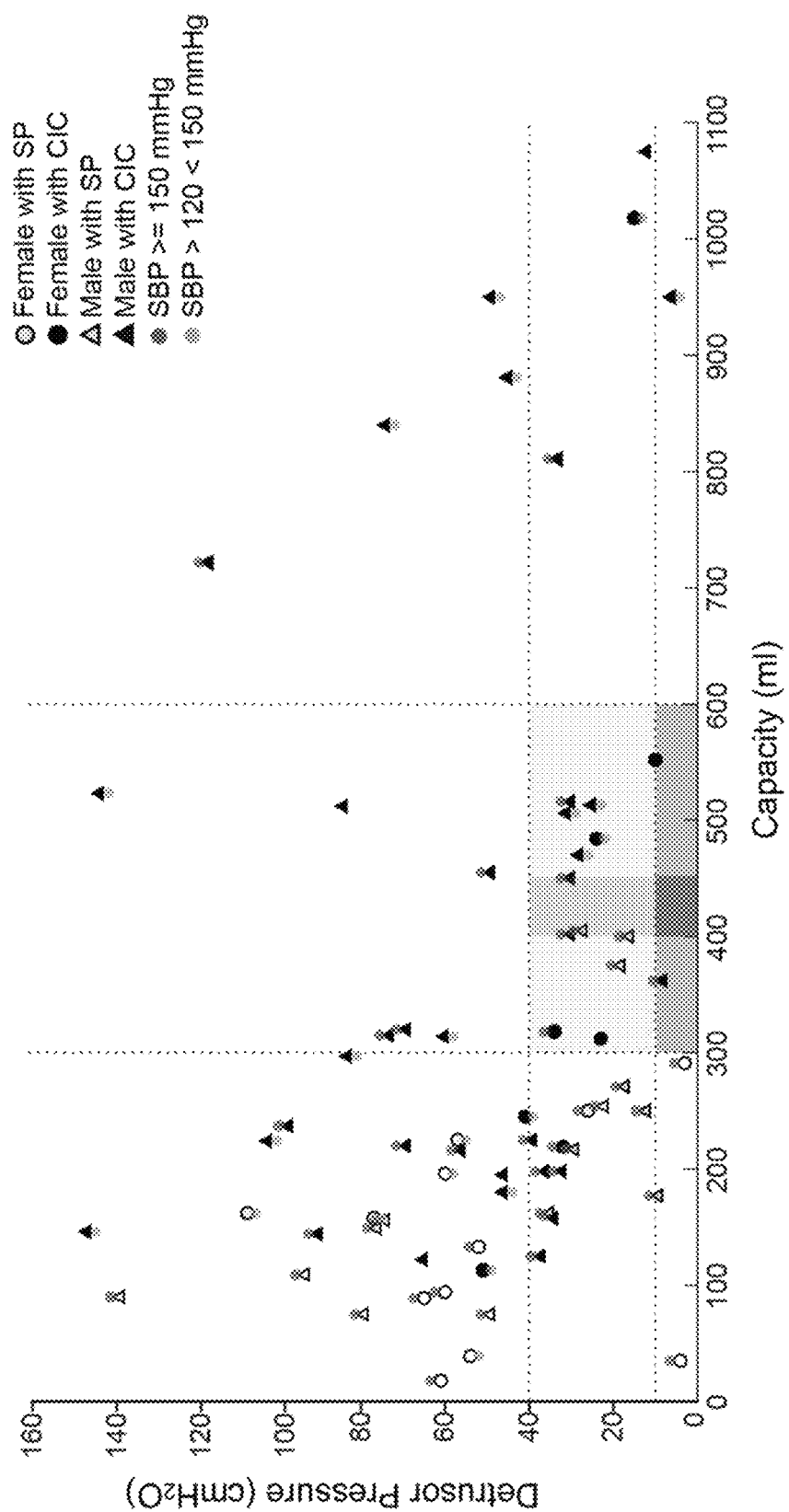
FIG. 7A is a scatter plot illustrating the relationship between bladder capacity (ml) and detrusor pressure ($cmH_2O$), during filling cystometry, in which the majority of individuals have low bladder capacity (impaired bladder storage) and high detrusor pressure (can lead to deterioration of the upper urinary tract). Maximal filling pressure is indicated by the horizontal dashed line at 10 $cmH_2O$ and the upper threshold for detrusor leak point pressure is indicated by the dashed horizontal line at 40 $cmH_2O$. Vertical dashed lines indicate the recommended clinical reference range, per ICS standards, (300-600 ml, shaded beige) for bladder capacity, while the narrower shaded gray area reflects optimal storage capacity based upon average daily input/output using standard catheterization times. Systolic blood pressure (mmHg) values recorded at the time of maximum detrusor pressure in each participant are identified with pink or red circles on the corresponding data points if >120 mmHg or ≥150 mmHg, respectively, indicating elevated systolic blood pressure in response to bladder fullness. (CIC, clean intermittent catheterization; cm $H_2O$, centimeters of water; ICS, International Continence Society; ml, milliliters; mmHg, millimeters of mercury; SBP, systolic blood pressure; SP, suprapubic).

Lower Urinary Tract Function—Screening Profiles. As part of the urodynamic assessment, filling cystometry was conducted on 70 individuals during screening. A representation of the detrusor pressure-volume relationship and associated systolic blood pressure responses to bladder distention in each participant is plotted in FIG. 7A. Note that few participant data fall within the optimal range and most have elevated systolic blood pressures. While blood pressure was captured continuously during cystometry, the systolic blood pressure values superimposed on each data point represent the value obtained at maximum bladder capacity. The majority of participants (60%; n=24, suprapubic catheter; n=18 intermittent catheter) had bladder capacity values below the recommended clinical guidelines for volume (<300 ml, 300-600 ml range, shaded beige). Within this sub-cohort, 64% of these participants also had bladder pressures values above the recommended threshold (>40 cmH$_2$O per International Continence Society (ICS) guidelines; 36% suprapubic catheter; 28% intermittent catheterization). The greatest blood pressure responses at maximum capacity (>150 mmHg) were present in those using suprapubic catheters and having bladder capacity less than 300 ml (27% of all screening participants). The percentage of individuals from the screening cohort having bladder capacity and detrusor pressure within the recommended ranges was 20%, yet the vast majority of these individuals (86%) still presented with elevated blood pressure responses (>120 mmHg) at maximum capacity. Conversely, a subset of individuals (11%), all utilizing intermittent catheterization, had large bladder volumes above the upper limit of the recommended capacity range. Note that the total volume also includes any excess amount produced through diuresis and not solely infused volume. Total voiding efficiency (based off reflex void volume for those who leaked) for the entire screening cohort was low (36±20%).

Figures 7B, 7C:
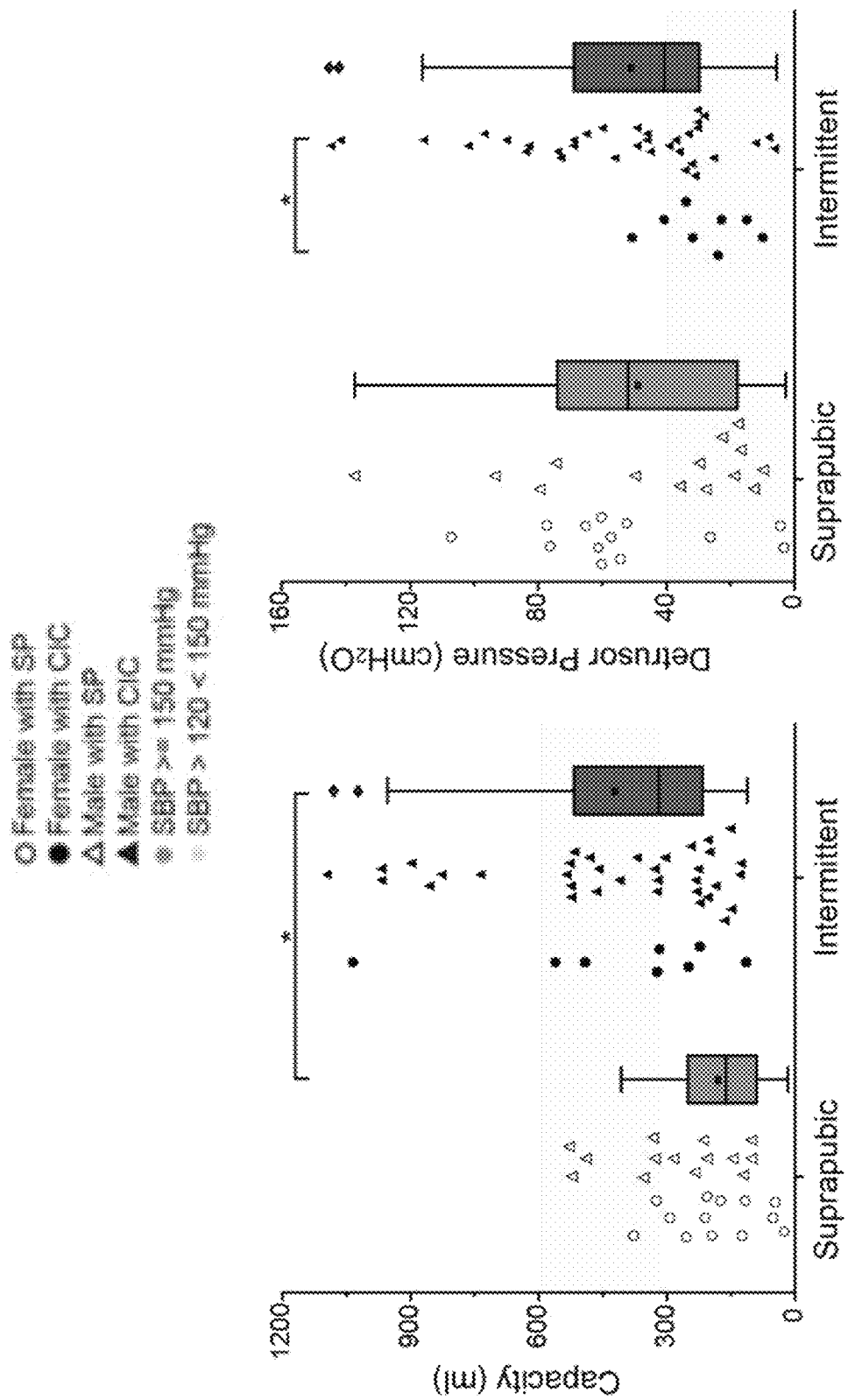
FIG. 7B is box plot illustrating the ranges of bladder capacity values of the screening participants, indicating low capacity values for those using suprapubic catheters. The horizontal lower, mid and upper lines of the boxes represent the 25th percentile, the median and the 75th percentile respectively. The square in the middle of each box represents the mean.
FIG. 7C is box plot illustrating detrusor pressure of the screening participants, indicating potential sex-related differences in pressure. The horizontal lower, mid and upper lines of the boxes represent the 25th percentile, the median and the 75th percentile respectively. The square in the middle of each box represents the mean.

In the overall cohort, those using intermittent catheterization had significantly greater capacity values relative to those using suprapubic catheters (419±271 ml versus 180±107 ml, respectively, p<0.0001) (FIG. 7B). While there were no significant differences in detrusor leak point pressure values between catheter groups overall (intermittent catheter, 51±33 cmH$_2$O; suprapubic catheter, 49±34 cmH$_2$O), females had significantly lower bladder pressure values compared to males (29±14 cmH$_2$O versus 56±35 cmH$_2$O, p<0.05) in the intermittent catheter sub-group (FIG. 7C). Blood pressure responses at maximum capacity were significantly greater in those using suprapubic catheters versus intermittent catheterization (161±18 mmHg versus 148±24 mmHg, p<0.05). There were no significant differences noted between males and females when evaluating overall capacity, total voiding efficiency, or blood pressure, nor within each catheter sub-group.

Figure 8A:
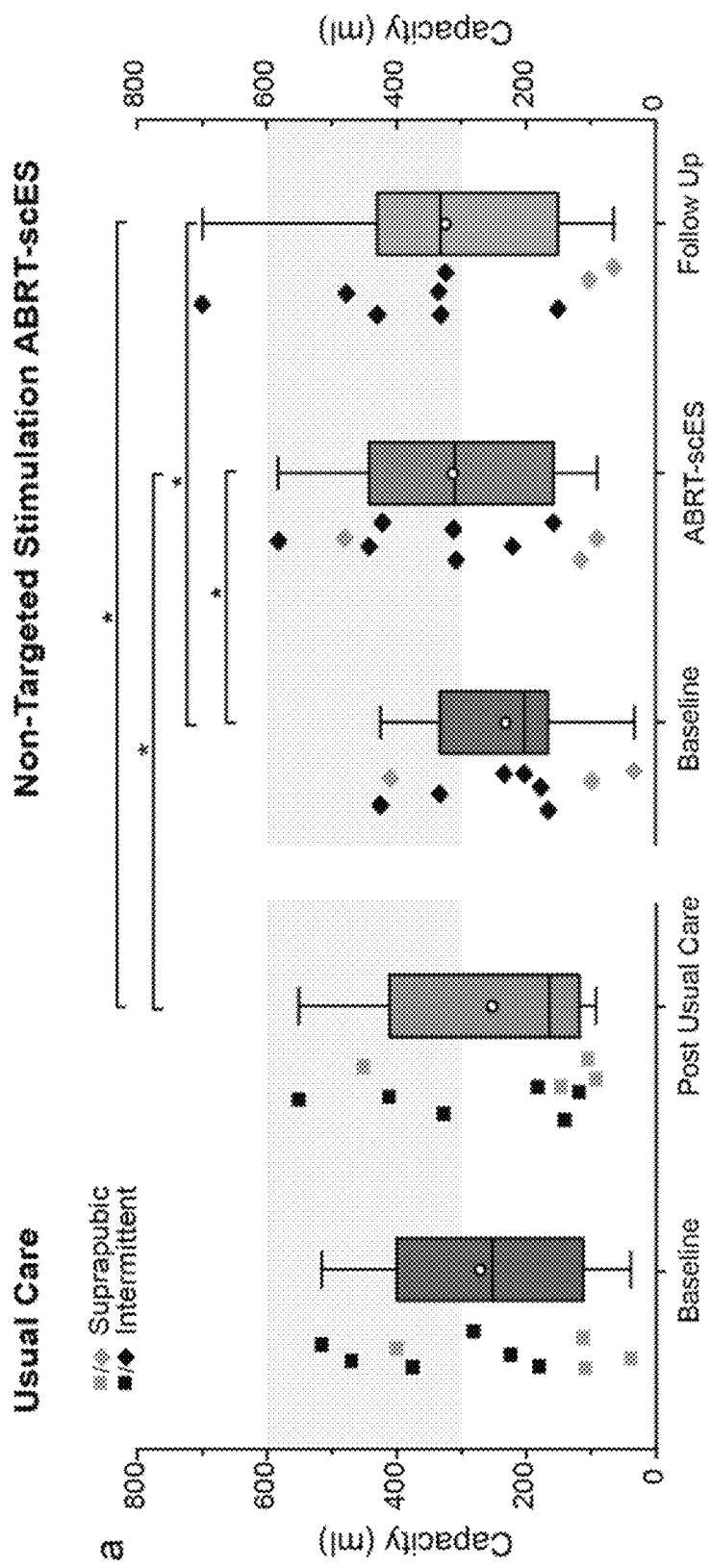
FIG. 8A is a box plot comparing bladder capacity ($cmH_2O$) in the usual care group at baseline relative to post-usual care (left two plots) and the in group receiving ABRT-scES (non-targeted stimulation for bladder) at baseline, post ABRT-scES, and at the 1-year follow-up time point (right three plots). These data illustrate the positive gains in bladder capacity in those receiving ABRT and electrical stimulation in combination. The shaded gray areas represent the clinical reference range for bladder capacity (300-600 ml). The horizontal lower, mid and upper lines of the boxes represent the 25th percentile, the median and the 75th percentile respectively. The circle in the middle of each box represents the mean.
Figure 8B:
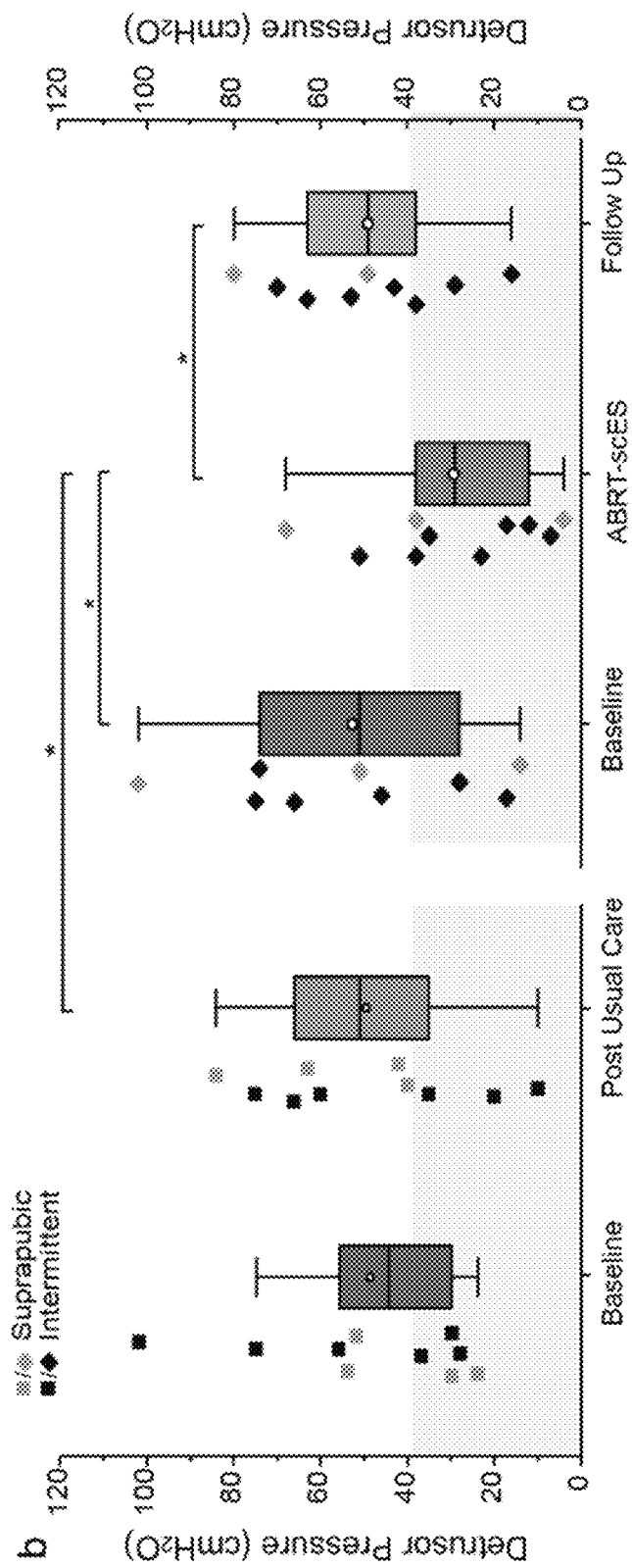
FIG. 8B is a box plot comparing detrusor pressure ($cmH_2O$) in the usual care group at baseline relative to post-usual care (left two plots) and the in group received ABRT-scES (non-targeted stimulation for bladder) at baseline, post ABRT-scES, and at the 1 year follow-up time point (right three plots). These data illustrate the positive gains (reduction) in detrusor pressure in those receiving ABRT and electrical stimulation in combination. The shaded gray areas represent the clinical reference range below the detrusor leak point pressure. The horizontal lower, mid and upper lines of the boxes represent the 25th percentile, the median and the 75th percentile respectively. The circle in the middle of each box represents the mean.
Figure 8C:
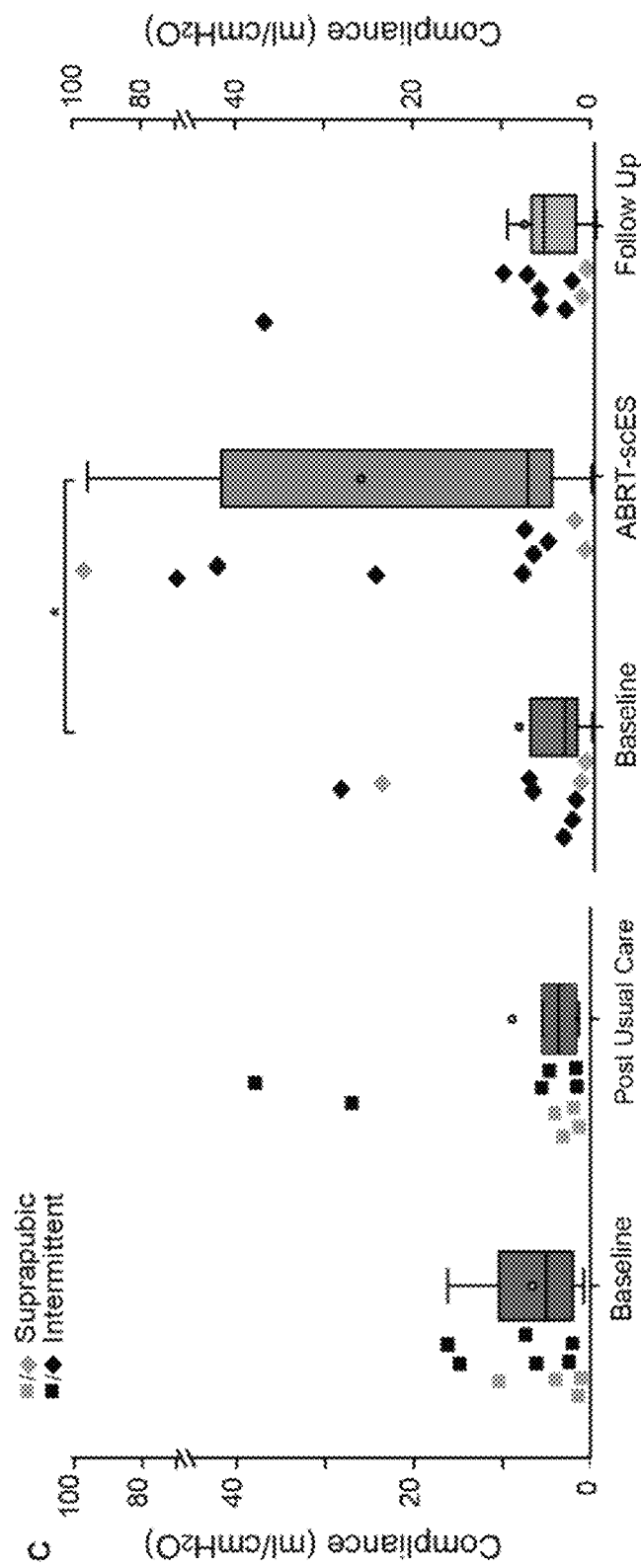
FIG. 8C is a box plot comparing compliance (ml/$cmH_2O$) in the usual care group at baseline relative to post-usual care (left two plots) and the in group received ABRT-scES (non-targeted stimulation for bladder) at baseline, post ABRT-scES, and at the 1 year follow-up time point (right three plots). These data illustrate the positive gains in bladder compliance in those receiving ABRT and electrical stimulation in combination. The horizontal lower, mid and upper lines of the boxes represent the 25th percentile, the median and the 75th percentile respectively. The circle in the middle of each box represents the mean.

Lower Urinary Tract Function—Non-targeted Epidural Stimulation and Usual Care. In the group receiving ABRT with scES (ABRT-scES), filling cystometry was conducted post-implantation and prior to training with scES, repeated just after completion of 160 sessions of training, and at the 1-year follow-up time point. Stimulation was used only during daily ABRT and was not used during any of the cystometrogram evaluations. Use at home during the one-year prior to follow-up assessment was variable and differed based upon sub-group (stand-scES only for the LT sub-group or CV-scES for the CV sub-group). A summary of the bladder capacity and pressure data for each group is represented in FIG. 8A-8C.

The usual care group received bladder assessments separated by a similar time interval as the scES group. Baseline bladder outcome variables were not statistically different between the usual care and ABRT-scES groups and there were no significant changes in bladder outcomes (capacity, detrusor pressure, compliance, total voiding efficiency, blood pressure responses to bladder distention) at the post-usual care time point relative to pre-usual care values (FIG. 8A). There was a significant improvement in bladder capacity following ABRT-scES relative to baseline (p<0.05) that maintained significance at follow-up (p<0.05) (Pre-training, 231±134 mL; Post-training, 313±166 mL; Follow-up, 324±201 mL) (FIG. 8A). Bladder capacity values for 60% of the participants reached ranges within the clinically recommended guidelines for appropriate bladder storage (range from 300 ml-600 ml) at both the post-training and follow-up time points.

Detrusor pressure was significantly decreased by the post-training time point (Pre-training, 53±30 cmH$_2$O; Post-training, 29±21 cmH$_2$O; p<0.01) with the majority of participants (80%) having detrusor leak point pressure below the clinically recommended threshold of 40 cmH$_2$O (FIG. 8B), values above which can lead to upper and lower tract deterioration. However, at the 1-year follow-up time point, detrusor pressure was significantly elevated relative to post-training values (49±20 cmH$_2$O, p<0.01), and was comparable to pre-training baseline (p>0.05). Similar to the post-training improvements in bladder capacity and pressure, bladder compliance, which evaluates the relationship between the change in bladder volume and change in detrusor pressure, was significantly improved post-training relative to baseline (p<0.01) (FIG. 8C), but reverted to baseline values by the 1-year follow-up time point.

Systolic blood pressure responses to bladder distention did not differ following ABRT-scES training (Baseline=131±15 mmHg versus Post-training=136±14 mmHg), nor were there any significant changes at follow-up relative to baseline or post-training values. Furthermore, an evaluation of systolic blood pressure changes from the pre-fill values (catheters in place) to the values captured at the point of maximum bladder capacity during the same study at both the baseline and post-training time points indicate that ABRT-scES did not attenuate bladder-distention associated increases in systolic blood pressure (Baseline change, 22±20 mmHg; Post-training change, 25±11 mmHg). No significant training-induced blood pressure differences were noted between intervention groups (LT-scES versus CV-scES).

Those receiving ABRT-scES had a significant improvement change in bladder capacity (70±83 mL, p<0.05) and detrusor pressure (reduction) (−22±cmH$_2$O, p<0.05) following training relative to those in usual care (−19±71 mL; 1±24 cmH$_2$O), as well as a significant improvement change in capacity (102±120 mL, p<0.05) at the 1-year follow-up time point relative to post-usual care (FIGS. 8A and 8B). In terms of blood pressure responses, a comparison between the post-training/post-usual care time points revealed that the ABRT-scES group had significantly lower systolic and diastolic blood pressure responses to bladder distention than the usual care group (p<0.01 and p<0.01, respectively).

Since collectively, there was a gain in capacity and a reduction in pressure in the ABRT-scES cohort, sub-group (n=6, LT; n=4, CV) training effects in relation to bladder outcomes were also evaluated. All baseline bladder and blood pressure outcome measures between the two scES training interventions were similar. There were no significant differences between the two different types of scES interventions at the post-training time point (Capacity=LT, 301±176 ml versus CV, 331±175 mL; Pressure=LT, 26±13 cmH$_2$O versus CV, 34±31 cmH$_2$O nor at follow-up (Capacity=LT, 342±214 ml versus CV, 289±208 mL; Pressure=LT, 41±17 cmH$_2$O versus CV, 64±19 cmH$_2$O).

The emptying phase of bladder function was assessed at the end of the filling phase or when the participant indicated a strong desire to void, typically reported as fullness in lower abdominal region. In total, 4 participants (2 AIS A, 2 AIS B) in the ABRT-scES group demonstrated the ability to voluntarily void with intent during this study. One participant (AIS b) was able to partially empty her bladder at all three time points and thus, a uroflow was conducted prior to catheter placement and filling. At post-training, the maximum flow rate (Qmax) during emptying was 2.0 ml/sec (12% VE). Note that the expected value for Qmax in females younger than 40 years of age is >22.0 ml/sec. Another participant (AIS B) was able to partially void voluntarily at the post-training (11.1% VE) and follow-up (36% VE) time points. Two other participants (both AIS A) voided at the post training time point (8.5% VE), and at the follow-up time point (17.2% VE), respectively. All 4 of these participants had distinct sensations of bladder fullness (first sensation of filling, first desire, strong desire) guiding their report of the need to empty and their intent during the void attempt. Voluntary voiding in these instances was generated from a low-pressure filling volume and distinct from a reflexive leak, which often occurred in response to an elevation in detrusor pressure overriding the pressure generated at the bladder outlet. In the overall ABRT-scES cohort, there were no significant changes in total voiding efficiency values from pre-training (23±27% VE) to post-training (26±31% VE) nor from post-training to follow-up (24±24% VE). No significant differences were found amongst the ABRT sub-groups (LT vs CV) at any of the assessment time points. None of the individuals (7 AIS A; 3 AIS B) in the usual care group were able to void voluntarily during testing.

Targeted Epidural Stimulation—Bladder Mapping. The identification of stimulation parameters for activation of spinal neural circuits to promote appropriate bladder capacity with low detrusor pressure and timely elimination of urine was conducted in two adult male participants. Both individuals were already implanted with a 16-electrode array (Medtronic 5-6-5, Minneapolis, MN) at the level of the lumbosacral spinal cord and were classified as motor complete SCI (partial preservation of sensation, but not motor, below the level of injury, as assessed according to the International Standards for Neurological Classification of SCI) at the time of enrollment (FIG. 6). Participant B21 was 32 years of age, 10 years post-C5 injury, and Participant B07 was 33 years of age, 12 years post-T1 injury at the time of enrollment. Both participants used clean intermittent catheterization as their daily method of bladder emptying.

Stimulation parameters (anode-cathode assignment, intensity, frequency, and pulse width) were adjusted during a lab-based cystometrogram study to optimize bladder capacity and voiding efficiency as well as cardiovascular responses to bladder distention. The investigation began with an evaluation of bladder compliance based upon volumetric capacity. The goal for capacity-scES was to target volumes between 400-500 mL, within the ICS clinical guideline values for optimal capacity for individuals performing clean intermittent catheterization 4-6 times per day (based upon average fluid intake). Also targeted pursuant to ICS guidelines were filling pressures (<10 cmH$_2$O for volumes up to 300 mL and <15 cmH$_2$O for volumes up to 500 mL) to improve overall bladder compliance and detrusor leak-point pressures (<40 cmH$_2$O). Maintaining normative systolic pressures during filling, within a range of 110-120 mmHg, was a further goal.

Figure 9:
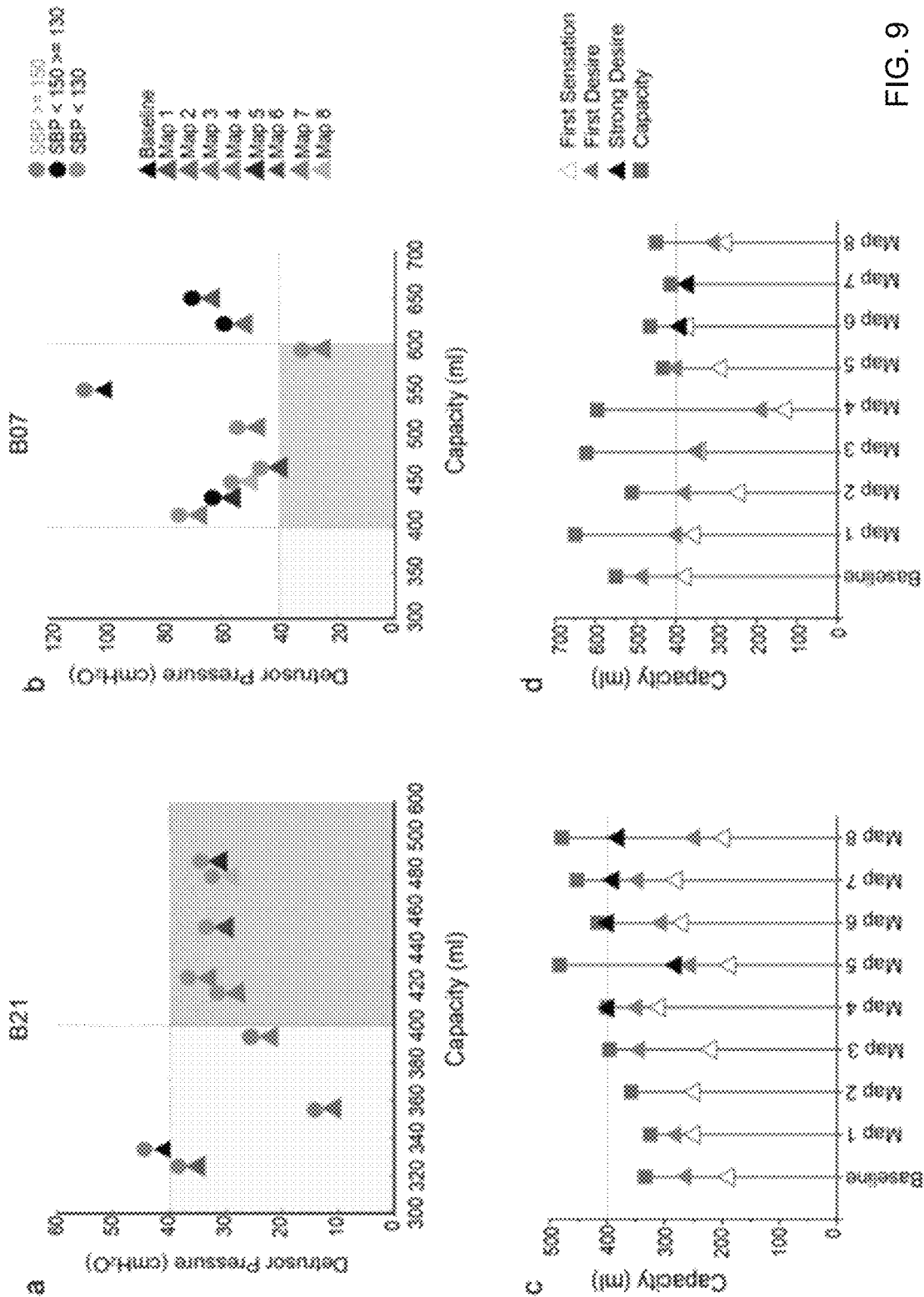
FIG. 9 depicts targeted epidural stimulation for bladder function. Bladder volume (ml) versus detrusor pressure ($cmH_2O$) scatter plots from participant B21 (Panel A) and B07 (Panel B) are shown at baseline and during mapping studies with scES configured for bladder and cardiovascular function. The highest systolic blood pressure (SBP) values during cystometry (bladder filling) were categorized into three groups and superimposed on the urodynamic outputs. The gray shaded areas indicate the normative relationship between bladder volume (300-600 ml) and detrusor pressure (<40 $cmH_2O$). Mapping targeted capacity above 400 to 500 mL, but not greater than 600 ml and leak point pressure below 40 $cmH_2O$. Mapping identified parameters that promoted optimal bladder compliance and normalized blood pressure in both participants. The relationship between maximum bladder capacity and sensations of filling (first sensation, first desire, and strong desire to void) during each mapping session is provided for participant B21 (Panel C) and B07 (Panel D). For participant B21, as maximum bladder capacity reaches the target values, sensations of filling become distinct for each category, while for B07, there is an earlier awareness of bladder sensations. (map, mapping session).

Urodynamics was conducted without scES prior to mapping (baseline value, FIG. 9). In participant B21, bladder capacity (BC)-scES mapping (8 sessions) identified parameters that achieved the target volume while reducing maximum detrusor pressure with cardiovascular (CV)-scES parameters preventing systolic increases in blood pressure by the 4th mapping session (FIG. 9, Panel A). In participant B07, BC-scES mapping identified specific parameters that reduced high detrusor pressure, while specific CV-scES parameters lowered maximum systolic blood pressure by the 3rd mapping session (FIG. 9, Panel B). Furthermore, sensations of bladder filling were used, when present, to guide mapping studies. Participant-reported sensations of fullness during bladder filling were recorded. FIG. 4, Panels C and D, reflect the maximum cystometric capacity values attained for each mapping session conducted and the associated sensations reported during filling. For participant B21 mapping, as the targeted bladder capacity was reached, all filling sensations were present and distinct, with less overlap and more separation during an extended filling duration (FIG. 9, Panel C). Thus, BC-scES promoted bladder compliance, accommodating a larger capacity relative to no scES (<200 cc) where sensations were less distinct. For participant B07, an increased awareness developed to bladder filling at lower volumes during BC-scES relative to no scES and early mapping, which likely contributed to the desire to empty, avoiding higher volumes and over-distention (>600 mL) (FIG. 9, Panel D). Sensations without scES and during initial mapping were timed with blood pressure elevation at maximum bladder capacity. Thus, with both BC-scES and CV-EpiStim, B07 had earlier awareness and sensations of fullness occurring within normalized ranges resulting in less over-distention and lowered maximum systolic blood pressure, evident in FIG. 9, Panel B.

Figure 10A:
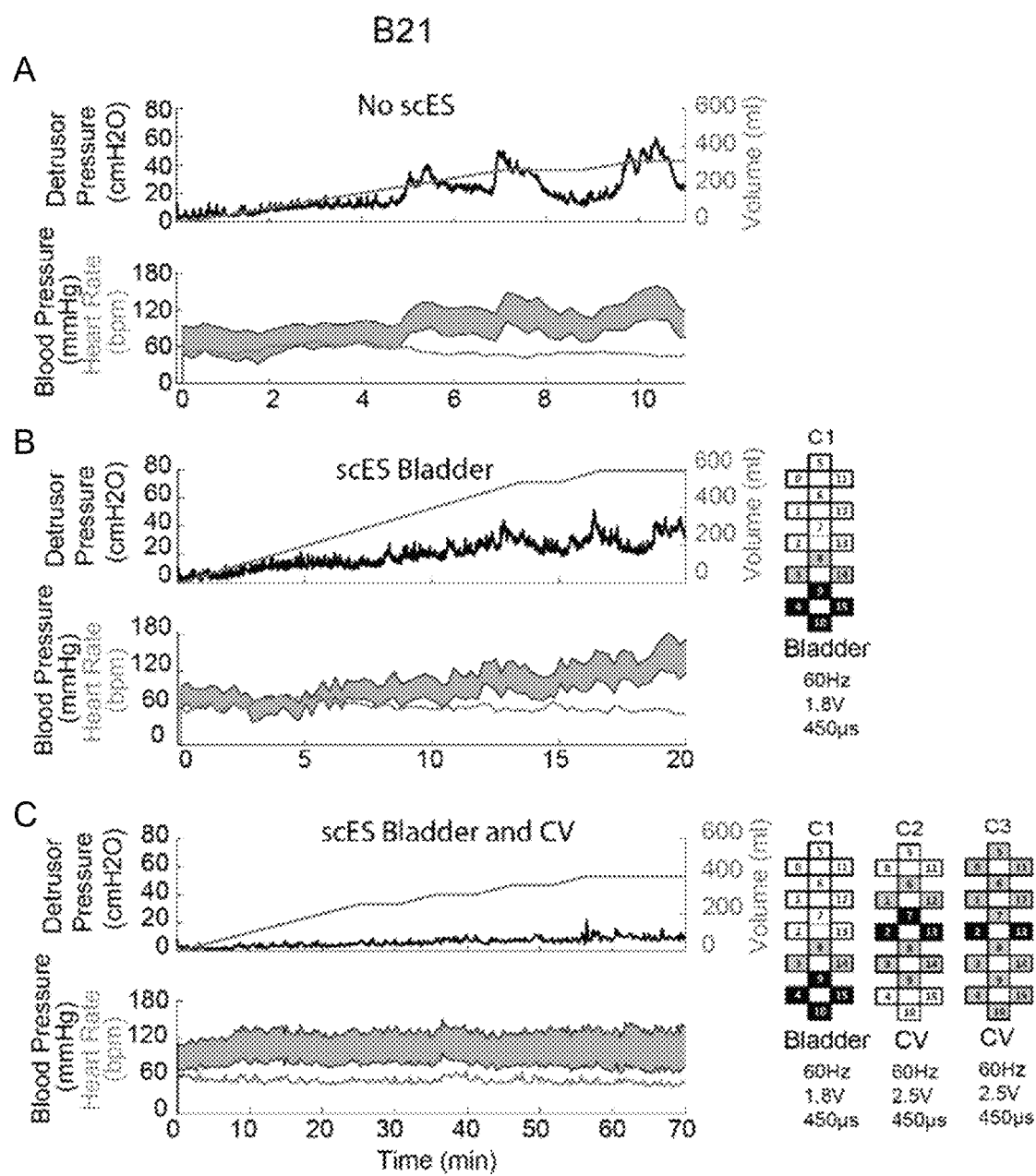
FIG. 10A illustrates intersystem stimulation (integrating epidural stimulation parameters for LUT and cardiovascular function) for participant B21. Representative cystometry traces including detrusor pressure ($cmH_2O$), blood pressure (mmHg) and heart rate (HR, red) responses over time without scES (Panel A), with BC-scES (Panel B), and with BC-scES+CV-scES (Panel C). BC-scES alone improved or maintained bladder capacity within target ranges (400-500 mL) with a reduction in detrusor pressure. However, maintenance of both blood and bladder pressures within clinically acceptable ranges during bladder filling required BC-scES and CV-scES. Black electrodes represent cathode stimulating electrodes, gray electrodes represent anodes, and white electrodes are inactive. (bpm, beats per minute; CV, cardiovascular; C, cohort; Frequency of the stimulation (Hz); Intensity is represented in volts (V) for B21; Pulse width is in microseconds (μs), BC-scES, bladder capacity-spinal cord epidural stimulation, CV-scES, cardiovascular spinal cord epidural stimulation, Time in minutes (min)).
Figure 10B:
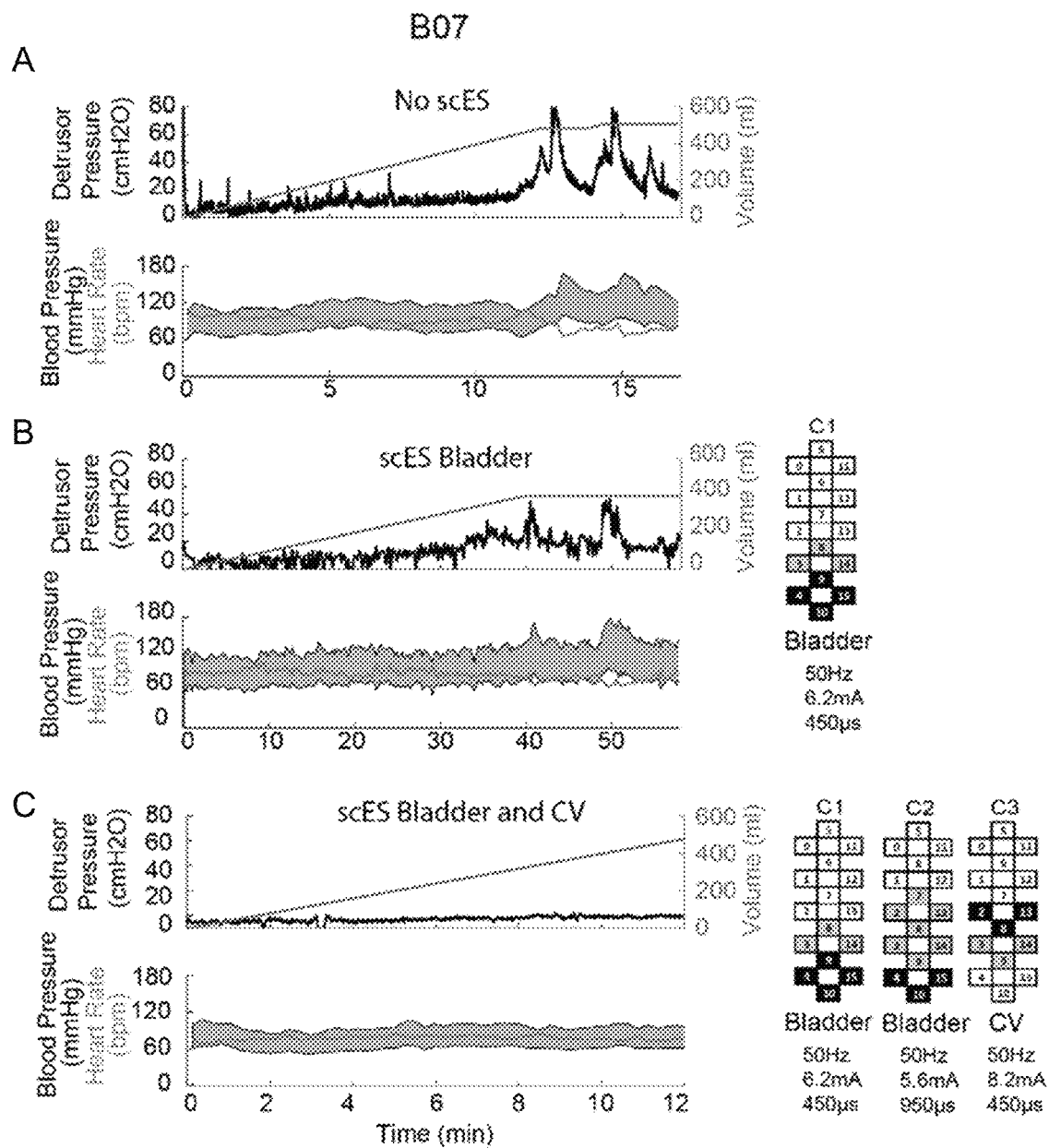
FIG. 10B illustrates intersystem stimulation for participant B07. Representative cystometry traces including detrusor pressure ($cmH_2O$), blood pressure (mmHg) and heart rate (HR, red) responses over time without scES (Panel A), with BC-scES (Panel B), and with BC-scES+CV-scES (Panel C). BC-scES alone improved or maintained bladder capacity within target ranges (400-500 mL) with a reduction in detrusor pressure. However, maintenance of both blood and bladder pressures within clinically acceptable ranges during bladder filling required BC-scES and CV-scES. Black electrodes represent cathode stimulating electrodes, gray electrodes represent anodes, and white electrodes are inactive. (bpm, beats per minute; CV, cardiovascular; C, cohort; Frequency of the stimulation (Hz); Intensity is represented in milliamperes (mA) for B07; Pulse width is in microseconds (μs), BC-scES, bladder capacity-spinal cord epidural stimulation, CV-scES, cardiovascular spinal cord epidural stimulation, Time in minutes (min)).

Typical examples of detrusor and blood pressure responses during filling cystometry without and with targeted scES are provided in FIGS. 10A and 10B. Without scES, detrusor responses to increased volume exhibited instability marked by sharp and sustained increases in pressure in both participants (Panel A in both FIGS. 10A and 10B). Additionally, detrusor pressure rose above clinically-recommended thresholds for bladder filling and detrusor leak-point pressures. Furthermore, timed with each non-voiding contraction was an increase in systolic blood pressure, which remained elevated and outside the normative reference range, resulting in cessation of bladder filling, removal of residual volume, and a subsequent return to pre-fill arterial pressure values. Such instability in both systolic and detrusor pressures limit bladder compliance, as evidenced by repeated reflexive contractions resulting in incontinence. Targeting electrodes at the caudal array in participant B21 (FIG. 10A, Panel B) resulted in an improvement in overall storage parameters, without incontinence. Although maximum detrusor pressure decreased from baseline, high systolic blood pressure persisted with the increase in capacity, resulting in cessation of the filling cycle. Coupling BC-scES with CV-scES (mid-array electrodes—based upon cardiovascular mapping for a prior study) allowed detrusor pressure to remain low during filling, reaching optimal bladder capacity and maintenance of blood pressure within target ranges (FIG. 10A, Panel C). For participant B07, while capacity was within normative ranges, BC-scES at the caudal array was ineffective for mitigating elevation in systolic blood pressure and detrusor pressure (FIG. 10B, Panel B). Integrating stimulation parameters targeted for CV-scES with dually paired BC-scES (addition of a wider pulse width cohort was necessary) resulted in a suppression of detrusor instability and maintenance of capacity under low pressure filling while simultaneously controlling systolic blood pressure responses to bladder distention (FIG. 10B, Panel C).

Figure 11A:
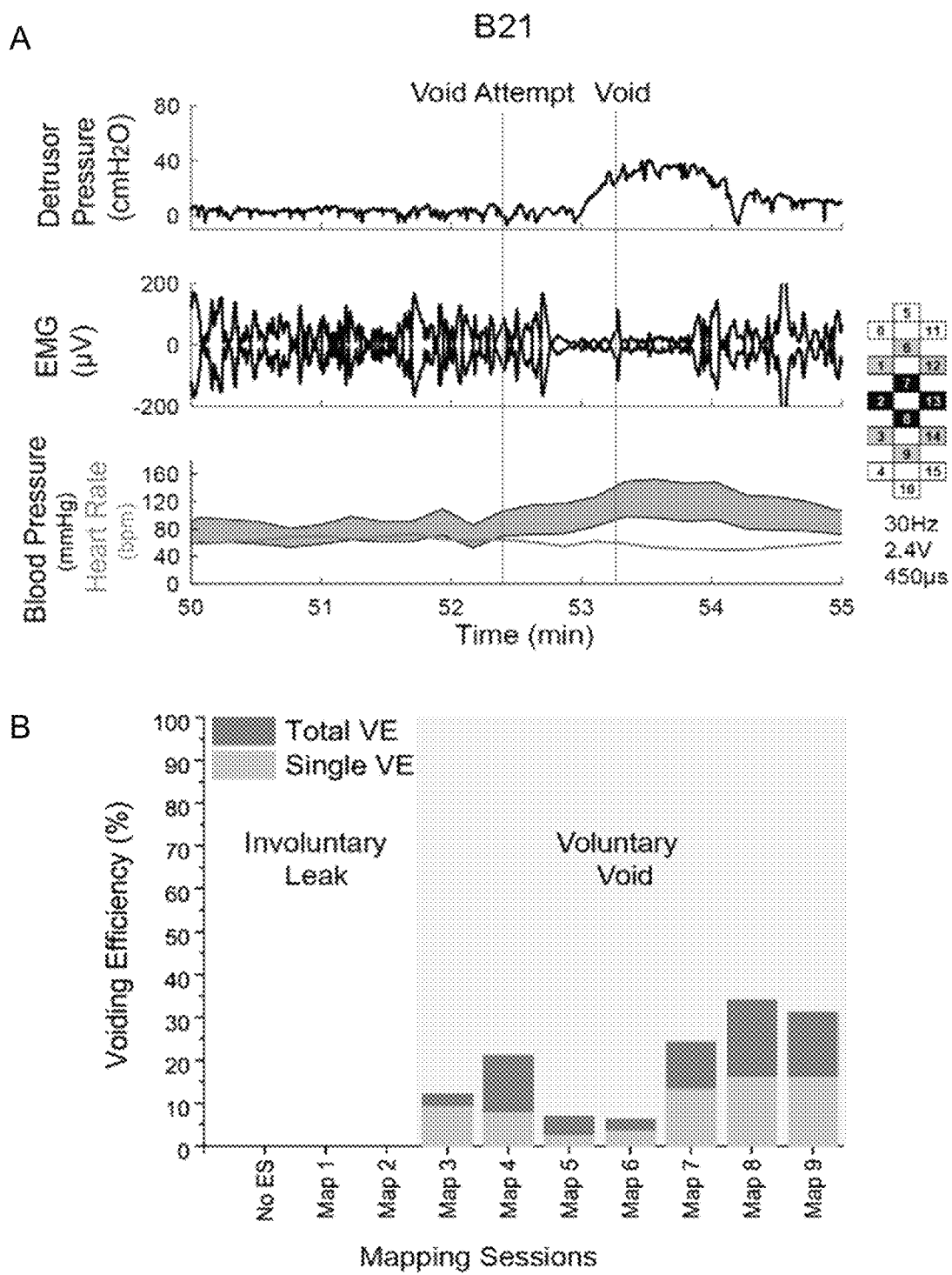
FIG. 11A illustrates targeting voiding with epidural stimulation for participant B21. Example voluntary voiding traces demonstrates a more synchronized detrusor-sphincter relationship resulting in effective emptying (note that a uroflow was not tested in the mapping environment and the EMG displayed reflects the linear envelope of the signal) (Panel A). A blood pressure response occurred beginning with participant B21's void attempt (start indicated with first vertical line in Panel A), followed by a return to baseline values once voiding initiated (indicated with second vertical line in Panel A), likely reflective of the participant's effort to empty. The voiding efficiency for a single maximum voluntary void event [(void volume/volume infused)*100)] is provided (light gray) in Panel B as well as the total voluntary voiding efficiency [(total void volume/total bladder capacity)*100] per mapping session (dark gray). Note that reflexive leaks were involuntary events. (bpm, beats per minute; $cmH_2O$, centimeters of water; Frequency of the stimulation (Hz); Intensity is represented in volts (V) for B21; map, mapping session; mmHg, millimeters of mercury; Pulse width is in microseconds (μs), Time in minutes (min); VE, voiding efficiency).
Figure 11B:
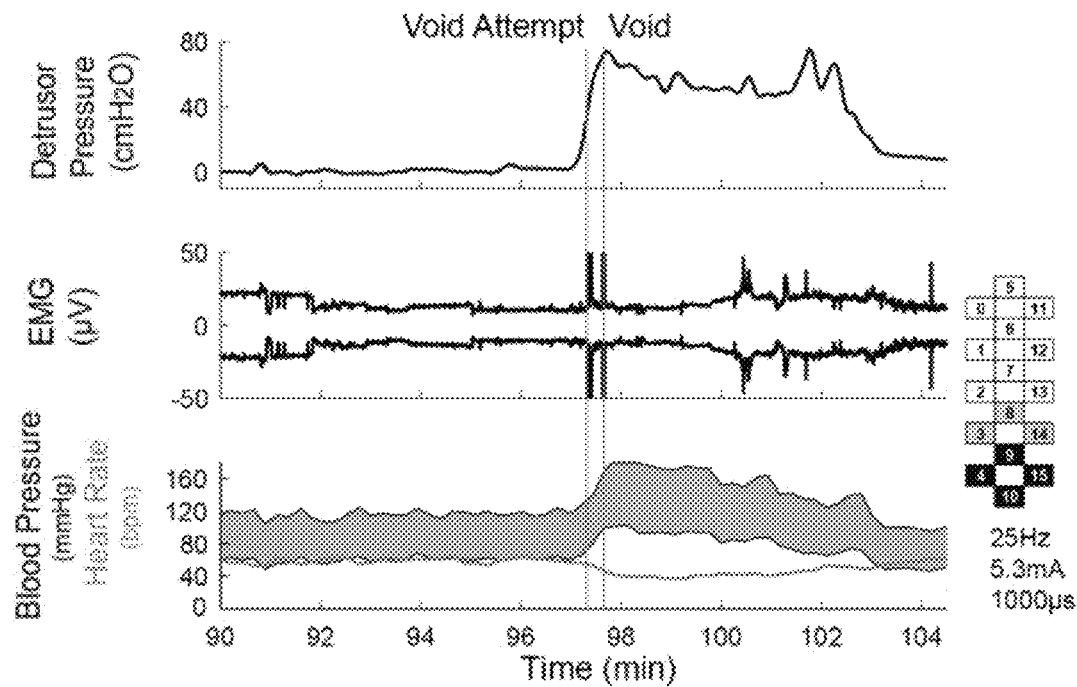
FIG. 11B illustrates targeting voiding with epidural stimulation for participant B07. Example voluntary voiding traces demonstrates a more synchronized detrusor-sphincter relationship resulting in effective emptying (note that a uroflow was not tested in the mapping environment and the EMG displayed reflects the linear envelope of the signal) (Panel A). A blood pressure response occurred beginning with participant B07's void attempt (start indicated with first vertical line in Panel A), followed by a return to baseline values once voiding initiated (indicated with second vertical line in Panel A), likely reflective of the participant's effort to empty. The voiding efficiency for a single maximum voluntary void event [(void volume/volume infused)*100)] is provided (light gray) in Panel B as well as the total voluntary voiding efficiency [(total void volume/total bladder capacity)*100] per mapping session (dark gray). Note that reflexive leaks were involuntary events. (bpm, beats per minute; $cmH_2O$, centimeters of water; Frequency of the stimulation (Hz); Intensity is represented in milliamps (mA) for B07; map, mapping session; mmHg, millimeters of mercury; Pulse width is in microseconds (μs), Time in minutes (min); VE, voiding efficiency).
Figure 11B:
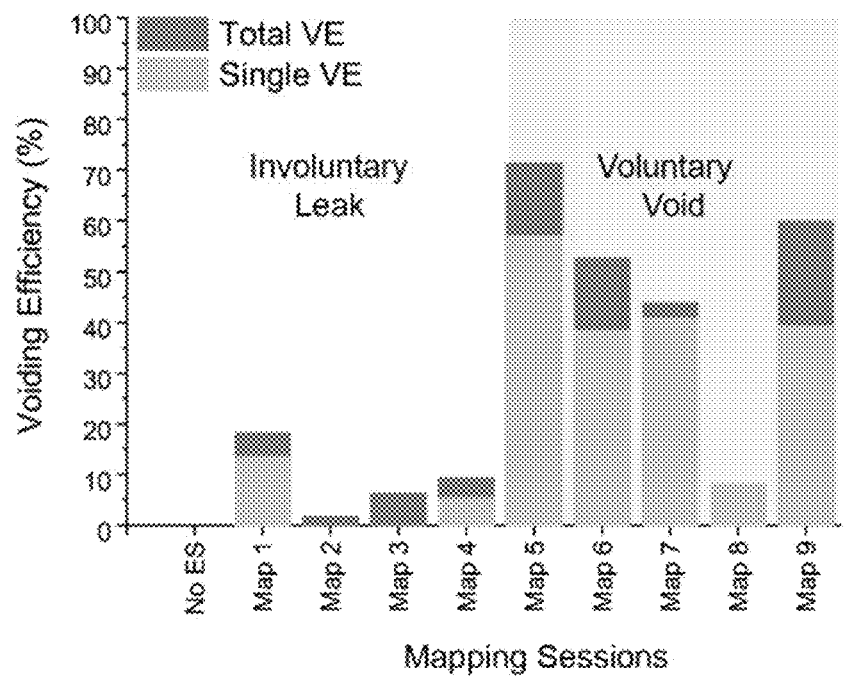

Subsequent mapping for bladder voiding efficiency (BVE)-scES was evaluated during cystometry at 80% of filling capacity (FIGS. 11A and 11B). Voiding was not achieved without scES in either participant. During initial mapping sessions with BVE-scES and in combination with void attempts, either no urine flow occurred, or an involuntary reflexive detrusor contraction occurred between attempts producing a low leak volume (participant B07) (FIG. 11A, Panel B). Voluntary attempts in combination with scES achieved partial emptying in both participants when timed to intent and desire to void with the sensation of bladder fullness. Example cystometrogram traces for B21 and B07 are provided in Panel A of FIGS. 11A and 11B, respectively, demonstrating the generation of a detrusor contraction and concurrent relaxation of the sphincter during voiding. Importantly, the void is timed close to the initiation of attempt, generating a detrusor contraction from a low-pressure baseline and subsequent return to baseline post-void. In both participants, BVE-scES mapping identified configurations that were frequency and intensity dependent, and distinct from BC-scES, with voiding occurring between 25-30 Hz and storage 50 Hz or above.

DISCUSSION. In the screening cohort diverse urological profiles were observed after SCI. The majority of those individuals' bladder function can be characterized as having low bladder capacity with high detrusor leak point pressure. Furthermore, most individuals, regardless of bladder management method (suprapubic vs intermittent catheterization) had elevated systolic blood pressure in response to bladder distention, suggesting a greater inter-dependent relationship between these two autonomic systems.

Critical to ensuring the long-term safety of the upper and lower urinary tract is the ability to achieve and maintain safe storage pressures. The use of indwelling suprapubic catheters as a method to continuously drain the bladder is an alternative method of emptying the bladder if self-intermittent catheterization poses a challenge for reasons including many of the following: limited hand function, spasticity and difficulty accessing the female urethra, lack of caregiver assistance, and/or incontinence. While suprapubic catheters are regarded by many consumers as a convenient, effortless alternative to a more demanding urethral catheterization management protocol, constant bladder drainage through an open conduit to an external storage bag impairs the physiological cyclic pattern of storage and emptying, resulting in poor functional compliance. As a result, minor increases in bladder volume, such as during cystometry, suprapubic clamping, catheter blockage, or catheter replacement may illicit autonomic dysreflexia. As expected, there was greater cardiovascular responsiveness to bladder distention during cystometry in this population. The rapid increase in systolic blood pressure is likely more dramatic in those utilizing suprapubic catheters, as these individuals represent a majority having cervical or high thoracic SCI, resulting in the loss of supraspinal regulation of spinal sympathetic activity and disrupted cardiovascular regulation. Bladder distention is one of the primary triggers of autonomic dysreflexia and while some individuals report not being symptomatic (i.e. during a suprapubic clamping regimen), they may be unaware they are experiencing significant elevations in systolic pressure, referred to as "silent AD." Such severe fluctuations in blood pressure pose a major limitation in the ability to recover bladder function long-term. In regard to those individuals with suprapubic catheters having bladder capacities within normative ranges, it is possible that some engaged in routine catheter clamping, a practice often utilized in an effort to preserve bladder capacity. Overall bladder self-care and hygiene, including routine suprapubic catheter replacement, caregiver availability to assist with catheter maintenance, inadequate perineal hygiene or hand washing that can lead to increased urinary tract infections, may also be contributing factors in the diverse urological outcomes evident in those using suprapubic catheters.

A select group of individuals was also found to have over-distended bladders, with high bladder volumes, characterized as areflexic (low detrusor tone). Oftentimes, a reduction in the standard frequency of daily and/or nightly catheterizations as a means to curtail emptying can contribute to bladder over-distention long-term. One such contributing factor is altered diurnal secretion of antidiurectic hormone after SCI, resulting in the incidence of polyuria (overproduction and/or passage of urine). The excessive urine production can further exacerbate an already demanding catheterization schedule and disrupt daily life. We have found that the mechanisms underlying SCI-induced polyuria are multifactorial, involving an interplay of various peptides involved in the physiological regulation of fluid balance, plasma volume, and overall urine output. Although not an underlying component in the population we assessed, the use of botulinum-A toxin injections into the detrusor muscle as an approach to reduce bladder over-activity by blocking parasympathetic neurotransmission, can lead to urinary retention and bladder over-distention primarily in those not adhering to a consistent intermittent catheterization schedule.

In terms of evaluating the impact of scES as intervention, the ability to harness existing spinal neural control mechanisms with devices for bladder control has continued to evolve over time, as the lumbosacral circuitry controlling the bladder remains intact after most SCI's. Some of the primary electrical stimulation approaches aimed at modulating bladder function have included stimulation of the spinal cord, select peripheral and sacral nerves, indirectly through the skin, as well as the bladder itself. In our center, the use of scES initially focused on modulating the excitability of spinal neural networks with the goal of enhancing stepping, standing, and voluntary movement in response to provided task-specific sensory cues in both complete and incomplete SCI. The integration of somatosensory and residual descending inputs to the spinal circuitry further contributed to unexpected gains in other physiological systems such as, bladder, sexual function, and temperature regulation. Despite the fact that the stimulation parameters were aimed at influencing the motor system and the execution of specific motor patterns, multiple autonomic improvements occurred.

In the non-targeted stimulation cohort, activation of lumbosacral spinal networks through ABRT-scES resulted in a significant improvement in bladder capacity and a significant reduction in detrusor leak point pressure, with mean values falling within recommended clinical guidelines. The finding that capacity remained significantly improved from baseline at the one-year follow-up time point is likely due to participant clearance for community integration and independent home-training after completion of the intervention phase, whereby they utilize scES for standing or CV function on a consistent basis, and thus continue to activate these overlapping circuits. Other factors related to urological care that cannot be controlled outside the research environment, such as medication usage which can impact detrusor contractility, may be why there was not a long-term continual improvement in detrusor pressure at the 1-year follow-up time point. These results support the effect of adaptive scES training-induced plasticity in the nervous system and the ability of the spinal cord to interpret and integrate distinct somatosensory cues associated with loading and/or autonomic inputs. A vesico-somatic interaction between the circuitries controlling bladder and locomotor function is also anticipated, as we have previously demonstrated that locomotor training alone was sufficient to induce significant improvements in multiple bladder parameters. It is not yet clear as to the overall impact on bladder function with scES targeting cardiovascular function alone since four participants received that intervention for this study. In this cohort, ABRT-scES did not attenuate peak systolic blood pressure in response to bladder distention, suggesting the critical role of task-specific stimulation and the need for identifying cardiovascular parameters during bladder filling.

Through targeted stimulation for the LUT in two participants, we identified participant-specific scES parameters in bladder mapping experiments that promoted overall bladder compliance while maintaining normotensive blood pressure during filling as well as parameters that enabled voluntary voiding. In support of these findings, the results of Study A demonstrated the efficacy of scES to excite the spinal cord circuitry at the lower lumbosacral region, which resulted in the facilitation of neural output to the bladder to improve emptying in a participant (AIS B) using an SP catheter. This configuration was then re-tested in four additional individuals (3 AIS A, 1 AIS B), already implanted with spinal cord epidural stimulators, improving bladder emptying in each participant (one participant also using an SP catheter), however, not to the degree as the original participant. Based on our previous mapping studies for motor control interventions, optimal configurations vary from individual to individual, necessitating participant-specific mapping. Individualized customization of the stimulation parameters was also necessary to selectively modulate and achieve optimal restoration of cardiovascular function. Excitation of the spinal cord with scES through appropriately selected stimulation parameters has the potential to modulate local spinal reflexes important for both storage and emptying. The additional improvements in sensory awareness (distinct from symptoms of autonomic dysreflexia) also suggest an activity-dependent reorganization of supraspinal centers, important for guiding voiding behavior, which is mediated by spinobulbospinal pathways. In both our recent cardiovascular and bladder studies, we have demonstrated that scES, in the absence of descending input, can modify the excitability of relevant spinal inter-neuronal pools allowing them to respond to peripheral autonomic input. The results of the bladder mapping portion of the study demonstrate that scES can be used to simultaneously and safely control urinary continence and voiding while managing distention-associated dysregulation of blood pressure. Importantly, these initial findings reveal the complex dynamics and interplay between sympathetic and parasympathetic circuitries that is being integrated and regulated within the spinal cord below the level of SCI. This spinal circuitry is driven by peripheral input and modulated by scES to effectively optimize both the state of bladder as well as systemic blood pressure. It is also likely, given the void intent results, that scES enhances the conduction properties of residual damaged or non-functional but anatomically intact long ascending/descending axons that are traversing across the spinal injured segment. In this manner, scES acting upon lumbosacral spinal neural networks can promote an increase in overall autonomic regulation sufficient to interact with appropriate sensory cues (e.g. from bladder distention) as well as engage descending supraspinal residual inputs (e.g. intent to void) to facilitate continued involvement of such networks to maintain target bladder compliance, initiate on-demand voiding, and regulate cardiovascular parameters during storage and emptying. Additional factors contributing to the scES-induced attenuation of autonomic dysreflexia associated with bladder distention seen during mapping may be indirectly linked with a suppression of C-fiber mediated bladder reflex activity as the detrusor smooth muscle becomes more compliant in response to mechanical stimuli and filling during scES. In a rodent model of SCI, such C-fiber bladder afferents (capsaicin-sensitive) have been implicated in the generation of detrusor over-activity and non-voiding contractions (primary triggers of autonomic dysreflexia) during the filling phase.

Given that the consequences of SCI affect multiple systems, this intervention has the potential to benefit other autonomic systems and dramatically impact quality of life. Furthermore, once a participant's device is programmed with effective stimulation programs, the ability for on-demand device use is key for initiating particularly timely tasks, such as voiding.

METHODS—Participants. A total of 82 individuals, 36±12 years of age (68% male, 32% female), with chronic SCI (C1-T12) are included in this study (FIG. 6). The observational data (screening) and usual care time points were obtained from participants enrolled in a research study conducted at the University of Louisville prior to receiving any intervention (IRB #16.0179, Task and Physiological Specific Stimulation for Recovery of Autonomic Function, Voluntary Movement and Standing using Epidural Stimulation and Training after Severe Spinal Cord Injury). Interventional epidural stimulation data were obtained from participants enrolled in studies at the University of Louisville investigating the effects of activity-based recovery in combination with scES on lower limb motor function (IRB #07.0066, Spinal Epidural Electrode Array to Facilitate Standing and Stepping in Spinal Cord Injury), cardiovascular function (IRB #13.0625, Recovery of Cardiovascular Function with Epidural Stimulation after Human Spinal Cord Injury), and bladder function (IRB #17.1024, NCT03452007, Task and Physiological Specific Stimulation for Recovery of Function after Severe Spinal Cord Injury: Functional Mapping with Lumbosacral Epidural Stimulation for Restoration of Bladder Function after Spinal Cord Injury).

As part of the interventional studies, a 16-electrode array (5-6-5 Specify, Medtronic, Minneapolis, MN) was surgically implanted at the T11-L1 vertebral levels over spinal cord segments L1-S1. The electrode lead was tunneled subcutaneously and connected to the pulse generator (RestoreADVANCED, Medtronic, Minneapolis, MN) placed ventrally in the abdomen. As part of a control/comparative cohort, 10 participants completed two Urodynamic assessments separated by the same time interval as the interventional cohort. This period was termed "usual care", as the participants continued their typical daily lives without any study-related change in routine (no intervention). This phase addresses whether there would be any inherent variability between two Urodynamic measurements within the same time interval as the interventional cohort receiving scES and training. Two adult males implanted with a 16-electrode array (Medtronic 5-6-5, Minneapolis, MN) at the level of the lumbosacral spinal cord also participated in the epidural mapping portion of this study targeting the bladder.

Clinical Evaluation. All research participants received a clinical evaluation prior to study participation to assess motor and sensory status. Two clinicians independently performed the International Standards for Neurological Classification of Spinal Cord Injury in order to classify participants' injuries using the ASIA (American Spinal Injury Association) Impairment Scale (AIS) (FIG. 6). A physical examination also was performed by a clinician for medical clearance, ensuring participants' safety using the following inclusion criteria: 1) stable medical condition; 2) no painful musculoskeletal dysfunction, unhealed fracture, contracture, pressure sore or urinary tract infection that might interfere with training; 3) no untreated psychiatric disorders or ongoing drug abuse; 4) clear indications that the period of spinal shock is concluded determined by presence of muscle tone, deep tendon reflexes or muscle spasms and discharged from standard inpatient rehabilitation; 5) non-progressive supra-sacral SCI; 6) bladder dysfunction as a result of SCI; and 7) epidural stimulator implanted at the lumbosacral spinal cord. None of the participants received Botox injections for management of bladder dysfunction during the course of the study and all participants were off anti-spasticity medication (e.g. Baclofen). Each participant also received a bladder/kidney Ultrasound at the time of enrollment and were medically cleared by both the study Urologist and study physician to participate in the research studies.

Activity-based recovery training. After implantation of the stimulator, 10 participants underwent a total of 160 sessions of activity-based recovery training (ABRT-scES). Six participants received alternating stand and step recovery-based training with scES. Stand training over-ground lasted 1 hour per session (5 sessions per week) and was always performed with spinal cord epidural stimulation using a custom designed standing apparatus comprised of horizontal bars anterior and lateral to the individual to provide upper extremity assistance and balance support. The individual was encouraged to stand for as long as possible throughout the training session, with the goal to stand for 60 minutes with the least amount of assistance. Seated resting periods occurred when requested by the individual. If, during standing, the participant's knees or hips flexed beyond the normal standing posture, external assistance to facilitate hip and knee extension was provided either manually by a trainer or by elastic cords, which were attached between the two vertical bars of the standing frame. Step training (1 hour, 5 sessions per week) was performed with body weight support (Innoventor, St. Louis, MO) on a treadmill and always with spinal cord epidural stimulation. Research participants stepped at body-weight load and speed adapted to achieve appropriate stepping kinematics and trainers provided manual assistance only when needed following standard locomotor training principles. Body-weight support was continuously reduced over the course of the training sessions as the ability to bear weight on the weight bearing limbs improved and manual facilitation was reduced as the ability to step independently improved. Four participants also underwent 160 sessions of cardiovascular (CV) training with scES which consisted of resting in a seated position for 2 hours with continuous blood pressure and heart rate monitoring. CV-scES configurations (anode and cathode electrode selection, voltage, frequency, and pulse width) were identified to maintain systolic blood pressure within a relatively stable blood pressure within non-injured defined normal ranges without eliciting motor activity. Participants in this non-loading group also received 80 sessions of voluntary training with scES (included in the 160 sessions) which consisted of practicing, in the supine position, unilateral leg flexion, ankle dorsiflexion and toe extension exercises with task-specific scES configurations on a daily basis (about 1 hour per session, 5 sessions per week).

Urodynamics. All urodynamics data were obtained from standard urodynamic evaluations with recommendations from the International Continence Society. Using the Aquarius® LT system (Laborie, Williston, VT), cystometry was performed in the supine position via a single sensor, dual channel catheter (7 Fr, T-DOC® Air-Charged™, Laborie, Williston, VT) with continuous filling of sterile, body-temperature water (37° C.) at a fixed slow rate of 20 mL/min. Abdominal pressure was measured via a rectal catheter (7 Fr, T-DOC® Air-Charged™, Laborie, Williston, VT). External anal sphincter electromyography (EMG) (Neotrode II, Laborie, Williston, VT) was recorded using surface patch EMG electrodes and a grounding pad was placed on a bony prominence, usually the hip or knee. Detrusor pressures were calculated by subtracting the intra-abdominal pressure from the intra-vesical pressure. Research participants were asked to cough to verify catheter positions and instructed to communicate sensations of a full bladder (first sensation); the desire to urinate (first urge to void); and strong desire to void and the feeling that voiding/leaking cannot be delayed (maximum capacity). The volume of water and bladder pressure were recorded. Uninhibited bladder contractions also were identified. All research participants ceased anticholinergics >24 hours prior to every urodynamics session. Note that spinal cord epidural stimulation was not used during cystometry.

Blood pressure (BP) and heart rate (HR) were obtained from the brachial artery, measured by oscillometric technique (Carescape V100, GE Healthcare, Milwaukee, WI), throughout the urodynamic session. Noninvasive continuous blood pressure was also measured from a finger cuff by plethysmographic technique (ADInstruments). It is important to note that instrumentation associated with the Urodynamic procedure can trigger autonomic dysreflexia, and thus baseline blood pressure was recorded in the seated position, supine and prior to catheter placement, prior to filling with catheters in place, continuously during testing, and post-testing, once catheters were removed and the participant returned to his or her wheelchair. Any signs and self-reported symptoms of autonomic dysreflexia were documented and observed throughout testing. Bladder filling was ceased if any of the following conditions were observed: 1) spontaneous urine leakage, 2) filling ≥600 ml or reaching maximum bladder capacity as evidenced by a rise in the compliance curve, 3) high intravesical pressure ≥40 cmH$_2$O or, 4) autonomic dysreflexia as evidenced by a sustained systolic blood pressure recording of ≥20 mm Hg from baseline and/or intolerable symptoms. A post-fill BP recording was captured to ensure BP values returned to baseline.

Bladder Mapping. Bladder mapping followed a human-guided interactive optimization approach where the experimental mapping process was decomposed into separate domains or subtasks in order to isolate parameters for storage, voiding and cardiovascular function. Since these domains are correlated, subsequent optimization tested and refined parameters concurrently in order to build a comprehensive framework for multi-system stimulation. Each participant completed a total of 17 sessions (8, storage; 9, voiding) mapping the detrusor and cardiovascular responses during both storage and emptying phases while scES parameters (anode, cathode selection; frequency and amplitude, and number of cohorts) were modulated to isolate successful intersystem configurations. Bladder mapping was initiated by selecting: 1) electrode configurations with cathodes positioned caudally, targeting the sacral micturition center (rostral and middle array locations were also tested in a congruent manner); 2) changes in detrusor pressure, sphincter activation/relaxation, and blood pressure responses were monitored while conducting a gradual ramp up of stimulation frequency and intensity; 3) a near-motor threshold stimulation amplitude that did not elicit direct lower limb movements was selected; 4) stimulation frequency and intensity were then modulated synergistically in order to isolate an optimal frequency that elicited an overall continuous detrusor pressure profile with a synchronized sphincter EMG pattern effective for bladder compliance; 5) frequency was kept fixed and amplitude adjusted in order to isolate an optimal intensity that drove voiding activity; and 6) electrode location and selection refinement was modified to adjust for sensory and autonomic symptoms during mapping. Mapping urodynamic studies were completed with at least two days apart.

Lower extremity and trunk EMG was monitored continuously throughout mapping to identify those parameters that modulate detrusor pressure and coordination with the external anal sphincter muscle (mirroring external urethral sphincter) and blood pressure, but do not elicit motor activity in the lower extremity or trunk. EMG was collected at 2,000 Hz using a 24-channel hard-wired AD board and custom-written acquisition software (Labview, National Instruments, Austin, TX, United States). EMG (MotionLab Systems, Baton Rouge, LA, United States) from the soleus, medial gastrocnemius, tibialis anterior, medial hamstrings, rectus femoris, and vastus lateralis using bipolar surface electrodes with fixed inter electrode distance. In addition, two surface electrodes were placed over the paraspinal muscles, symmetrically lateral to the epidural electrode array incision site. These two electrodes were used to record the stimulation artifact from the implanted electrode. EMG data were rectified and high-pass filtered at 40 Hz using Labview software customized by our laboratory.

Data Analysis. Bladder capacity was calculated as the volume of leaked or voided fluid plus any residual amount removed from the bladder. Voiding efficiency (VE) was calculated as: VE=[volume voided/(volume voided+residual volume)×100]. Compliance was calculated by dividing the volume change ($\Delta V$) by the change in detrusor pressure ($\Delta Pdet$) during that change in bladder volume and was expressed in ml/cm $H_2O$. The intravesical pressure (Pves) at which involuntary expulsion of water/urine from the urethral meatus was observed was considered the detrusor leak point pressure (DLPP). Maximum detrusor pressure (MDP) was identified as the peak detrusor pressure during the voiding phase of the cystometrogram. Detrusor pressures were calculated by subtracting the intra-abdominal pressure from the intra-vesical pressure. Note, if a participant did not leak during the fill cycle, MDP was used in place of DLLP. Filling sensations will be noted and are defined as: First sensation of fullness (FSF)—the first sense that there is fluid in the bladder; First desire (FD)—the feeling that you would void at the next convenient moment; Strong desire (SD)—a compelling need to void that is less comfortable to postpone; Capacity (C)—the feeling that voiding cannot be delayed any longer. All analyses were performed with customized software in MATLAB (MathWorks, Natick, MA)

Statistical Analysis. Continuous participant descriptors and bladder outcomes were tested for normality using the Kolmogorov-Simonov test for those showing large deviation. Variables that were found normally distributed were summarized with mean+SD and were compared with 2-sample t-test for 2 group comparisons or paired t-test for pre-post evaluations. Variables that failed the normality test were summarized with median and interquartile range and were compared with either the Rank Sum Test or the Signed Rank Test. Categorical variables were summarized with frequency count with associated percentage and compared with Chi-square tests or Fisher's exact test as appropriate. All tests were 2-sided with a significance level of 0.05. Statistical analyses were performed in SAS 9.4 (SAS Inc., Cary, NC).

Various aspects of different embodiments of the present disclosure are expressed in paragraphs X1, X2, X3, and X4 as follows:

X1: One embodiment of the present disclosure includes a method for improving lower urinary tract function in an individual, comprising: applying a first pattern of epidural electrical stimulation to the spinal cord of the individual at a location, frequency, and intensity sufficient to improve bladder storage.

X2: Another embodiment of the present disclosure includes a method for increasing bladder capacity in an individual, comprising: applying a first pattern of epidural electrical stimulation to the spinal cord of the individual at a location, frequency, and intensity sufficient to increase bladder capacity.

X3: Another embodiment of the present disclosure includes a method of controlling a cardiovascular state in an individual during one of bladder voiding and bladder filling, the method comprising: applying a first pattern of epidural electrical stimulation to the spinal cord of the individual at a location, frequency, and intensity sufficient to improve one of bladder voiding and bladder filling; and applying a second pattern of epidural electrical stimulation to the spinal cord at a location, frequency, and intensity sufficient to maintain a cardiovascular state of the individual within a predetermined range; and wherein the first pattern of epidural electrical stimulation and the second pattern of epidural electrical stimulation are applied simultaneously.

X4: Another embodiment of the present disclosure includes a method for improving lower urinary tract function in an individual, comprising: applying a first pattern of epidural electrical stimulation to the spinal cord of the individual at a frequency and intensity sufficient to reduce detrusor-external urethral sphincter dyssynergia.

Yet other embodiments include the features described in any of the previous paragraphs X1, X2, X3, or X4 as combined with one or more of the following aspects:

Wherein the method further comprises applying a second pattern of epidural electrical stimulation to the spinal cord at a location, frequency, and intensity sufficient to maintain a cardiovascular state of the individual within a predetermined range.

Wherein the cardiovascular state is one of heart rate and blood pressure.

Wherein the cardiovascular state is systolic blood pressure.

Wherein applying the second pattern of epidural electrical stimulation and applying the first pattern of epidural electrical stimulation occur simultaneously.

Wherein the first pattern and the second pattern are non-identical.

Wherein the first pattern and the second pattern are applied to the spinal cord at different locations.

Wherein the first pattern and the second pattern are applied to the spinal cord using Wherein the method further comprises applying a third pattern of epidural electrical stimulation to the spinal cord of the individual at a location, frequency, and intensity sufficient to improve bladder voiding, wherein applying the third pattern of epidural electrical stimulation occurs subsequent to applying the first pattern of epidural electrical stimulation, and wherein the second pattern of epidural electrical stimulation is applied during the application of the first pattern of epidural electrical stimulation and during the application of the second pattern of epidural electrical stimulation.

Wherein the method further comprises applying a third pattern of epidural electrical stimulation to the spinal cord of the individual at a location, frequency, and intensity sufficient to improve at least one of reflexive micturition and voluntary micturition, wherein applying the third pattern of epidural electrical stimulation occurs subsequent to applying the first pattern of epidural electrical stimulation, and wherein the second pattern of epidural electrical stimulation is applied during the application of the first pattern of epidural electrical stimulation and during the application of the second pattern of epidural electrical stimulation.

Wherein the method further comprises applying a third pattern of epidural electrical stimulation to the spinal cord of the individual at a location, frequency, and intensity sufficient to improve bladder voiding.

Wherein the method further comprises applying a third pattern of epidural electrical stimulation to the spinal cord of the individual at a location, frequency, and intensity sufficient to improve at least one of reflexive micturition and voluntary micturition.

Wherein applying the third pattern of epidural electrical stimulation occurs subsequent to applying the first pattern of epidural electrical stimulation.

Wherein the third pattern and the first pattern are non-identical.

Wherein the third pattern of epidural electrical stimulation is applied at a higher frequency than the first pattern.

Wherein the location is one or more spinal segments.

Wherein improving bladder storage comprises increasing bladder storage in the individual to within the range of 300 ml to 600 ml.

Wherein improving bladder storage comprises increasing bladder storage in the individual to within the range of 400 ml to 500 ml.

Wherein improving bladder storage comprises decreasing detrusor leak point pressure in the individual to <40 cmH$_2$O.

Wherein the method further comprises mapping lower urinary tract responses and cardiovascular responses upon applying epidural electrical stimulation to the spinal cord of the individual using multiple stimulation parameters, and wherein the first pattern of epidural electrical stimulation is determined at least in part on said mapping.

Wherein the method further comprises activity-based recovery training of the individual.

Wherein the epidural electrical stimulation is applied via an implanted electrode array.

Wherein the epidural electrical stimulation is applied via an implanted electrode array includes a plurality of electrodes.

Wherein at least one electrode used to apply the second pattern of epidural electrical stimulation is not used to apply the first pattern of epidural electrical stimulation.

Wherein at least one electrode used to apply the second pattern of epidural electrical stimulation is not used to apply the third pattern of epidural electrical stimulation.

Wherein the individual has an injury, neurological disorder, or disease state resulting in impaired lower urinary tract function.

Wherein the individual has a spinal cord injury.

Wherein the individual has a motor complete spinal cord injury.

The foregoing detailed description is given primarily for clearness of understanding and no unnecessary limitations are to be understood therefrom for modifications can be made by those skilled in the art upon reading this disclosure and may be made without departing from the spirit of the invention. While the present invention is discussed primarily in relation to individuals with SCI, it should be understood that embodiments are applicable to any individual with any ailment resulting in impaired LUT function, including but not limited to stroke, brain injury, cerebral palsy, neurological disorders or other injury, disorder, or disease state.

What is claimed is:

1. A method for improving lower urinary tract function in an individual, comprising:
    applying a first pattern of epidural electrical stimulation to the spinal cord of the individual at a location, frequency, and intensity sufficient to improve bladder storage; and
    applying a second pattern of epidural electrical stimulation to the spinal cord at a location, frequency, and intensity sufficient to maintain a cardiovascular state of the individual within a predetermined range;
    wherein applying the second pattern of epidural electrical stimulation and applying the first pattern of epidural electrical stimulation occur simultaneously; and
    wherein the method further comprises activity-based recovery training of the individual, including locomotor training.

2. The method of claim 1, wherein the cardiovascular state is one of heart rate and blood pressure.

3. The method of claim 1, wherein the first pattern and the second pattern are non-identical.

4. The method of claim 1, wherein the first pattern and the second pattern are applied to the spinal cord at different locations.

5. The method of claim 1, further comprising applying a third pattern of epidural electrical stimulation to the spinal cord of the individual at a location, frequency, and intensity sufficient to improve at least one of reflexive micturition and voluntary micturition,
    wherein applying the third pattern of epidural electrical stimulation occurs subsequent to applying the first pattern of epidural electrical stimulation, and
    wherein the second pattern of epidural electrical stimulation is applied during the application of the first pattern of epidural electrical stimulation and during the application of the third pattern of epidural electrical stimulation.

6. The method of claim 1, further comprising applying a third pattern of epidural electrical stimulation to the spinal cord of the individual at a location, frequency, and intensity sufficient to improve at least one of reflexive micturition and voluntary micturition.

7. The method of claim 6, wherein applying the third pattern of epidural electrical stimulation occurs subsequent to applying the first pattern of epidural electrical stimulation.

8. The method of claim 6, wherein the third pattern and the first pattern are non-identical.

9. The method of claim 6, wherein the third pattern of epidural electrical stimulation is applied at a higher frequency than the first pattern.

10. The method of claim 1, wherein the location is one or more spinal segments.

11. The method of claim 1, wherein improving bladder storage comprises increasing bladder storage in the individual to within the range of 300 ml to 600 ml.

12. The method of claim 1, wherein improving bladder storage comprises decreasing detrusor leak point pressure in the individual to <40 cm $H_2O$.

13. The method of claim 1, further comprising mapping lower urinary tract responses and cardiovascular responses upon applying epidural electrical stimulation to the spinal cord of the individual using multiple stimulation parameters, and wherein the first pattern of epidural electrical stimulation is determined at least in part on said mapping.

14. The method of claim 1, wherein the epidural electrical stimulation is applied via an implanted electrode array.

15. The method of claim 1, wherein the individual has an injury, neurological disorder, or disease state resulting in impaired lower urinary tract function.

16. The method of claim 15, wherein the individual has a spinal cord injury.

17. The method of claim 1, wherein the first pattern of epidural electrical stimulation is applied with a pulse width of about 450 microseconds.

18. The method of claim 1, wherein the activity-based recovery training step is performed before the applying steps and is performed in combination with the applying steps.

19. A method for increasing bladder capacity in an individual, comprising:
applying a first pattern of epidural electrical stimulation to the spinal cord of the individual at a location, frequency, and intensity sufficient to increase bladder capacity; and
applying a second pattern of epidural electrical stimulation to the spinal cord at a location, frequency, and intensity sufficient to maintain a cardiovascular state of the individual within a predetermined range; and
wherein the first pattern of epidural electrical stimulation and the second pattern of epidural electrical stimulation are applied simultaneously; and
wherein the method further comprises activity-based recovery training of the individual, including locomotor training.

20. A method of controlling a cardiovascular state in an individual during one of micturition and bladder filling, the method comprising:
applying a first pattern of epidural electrical stimulation to the spinal cord of the individual at a location, frequency, and intensity sufficient to improve one of micturition and bladder filling; and
applying a second pattern of epidural electrical stimulation to the spinal cord at a location, frequency, and intensity sufficient to maintain a cardiovascular state of the individual within a predetermined range; and
wherein the first pattern of epidural electrical stimulation and the second pattern of epidural electrical stimulation are applied simultaneously; and
wherein the method further comprises activity-based recovery training of the individual, including locomotor training.

21. A method for improving lower urinary tract function in an individual, comprising:
applying a first pattern of epidural electrical stimulation to the spinal cord of the individual at a frequency and intensity sufficient to reduce detrusor-external urethral sphincter dyssynergia; and
applying a second pattern of epidural electrical stimulation to the spinal cord at a location, frequency, and intensity sufficient to maintain a cardiovascular state of the individual within a predetermined range; and
wherein the first pattern of epidural electrical stimulation and the second pattern of epidural electrical stimulation are applied simultaneously; and
wherein the method further comprises activity-based recovery training of the individual, including locomotor training.

22. A method for improving lower urinary tract function in an individual, comprising:
applying a first pattern of epidural electrical stimulation to the spinal cord of the individual at a frequency and intensity sufficient to reduce detrusor over-activity; and
applying a second pattern of epidural electrical stimulation to the spinal cord at a location, frequency, and intensity sufficient to maintain a cardiovascular state of the individual within a predetermined range; and
wherein the first pattern of epidural electrical stimulation and the second pattern of epidural electrical stimulation are applied simultaneously; and
wherein the method further comprises activity-based recovery training of the individual, including locomotor training.

23. A method for improving lower urinary tract function in an individual, comprising:
applying a first pattern of epidural electrical stimulation to the spinal cord of the individual at a frequency and intensity sufficient to alleviate urinary incontinence; and
applying a second pattern of epidural electrical stimulation to the spinal cord at a location, frequency, and intensity sufficient to maintain a cardiovascular state of the individual within a predetermined range; and
wherein the first pattern of epidural electrical stimulation and the second pattern of epidural electrical stimulation are applied simultaneously; and
wherein the method further comprises activity-based recovery training of the individual, including locomotor training.

* * * * *